US008734525B2

(12) United States Patent
Behnam et al.

(10) Patent No.: US 8,734,525 B2
(45) Date of Patent: *May 27, 2014

(54) OSTEOINDUCTIVE DEMINERALIZED CANCELLOUS BONE

(75) Inventors: Keyvan Behnam, Red Bank, NJ (US);
Nanette Forsyth, Bayville, NJ (US);
James Russell, Little Silver, NJ (US);
John Winterbottom, Howell, NJ (US);
Todd Boyce, Matawan, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 347 days.

This patent is subject to a terminal disclaimer.

(21) Appl. No.: 12/140,025

(22) Filed: Jun. 16, 2008

(65) Prior Publication Data

US 2009/0155378 A1 Jun. 18, 2009
US 2014/0065239 A9 Mar. 6, 2014

Related U.S. Application Data

(63) Continuation-in-part of application No. 10/584,981, filed as application No. PCT/US2004/043999 on Dec. 31, 2004, now Pat. No. 8,328,876.

(60) Provisional application No. 60/986,843, filed on Nov. 9, 2007, provisional application No. 60/944,417, filed on Jun. 15, 2007, provisional application No. 60/533,537, filed on Dec. 31, 2003.

(51) Int. Cl.
*A61K 35/32* (2006.01)

(52) U.S. Cl.
CPC .................................. *A61K 35/32* (2013.01)
USPC .................. 623/23.63; 623/23.61; 623/16.11; 424/422; 424/423

(58) Field of Classification Search
None
See application file for complete search history.

(56) References Cited

U.S. PATENT DOCUMENTS

| | | | |
|---|---|---|---|
| 4,172,128 A | 10/1979 | Thiele et al. | |
| 4,294,753 A | 10/1981 | Urist | |
| 4,394,370 A | 7/1983 | Jefferies | |
| 4,430,760 A | 2/1984 | Smestad | |
| 4,440,370 A | 4/1984 | Rood | |
| 4,440,750 A | 4/1984 | Glowacki et al. | |
| 4,455,256 A | 6/1984 | Urist | |
| 4,472,840 A | 9/1984 | Jefferies | |
| 4,485,097 A | 11/1984 | Bell | |
| 4,563,350 A | 1/1986 | Nathan et al. | |
| 4,619,989 A | 10/1986 | Urist | |
| 4,657,548 A | 4/1987 | Nichols | |
| 4,678,470 A | 7/1987 | Nashef et al. | |
| 4,743,259 A | 5/1988 | Bolander et al. | |
| 4,755,184 A | 7/1988 | Silverberg | |
| 4,761,471 A | 8/1988 | Urist | |
| 4,774,228 A | 9/1988 | Seyedin et al. |
| 4,774,322 A | 9/1988 | Seyedin et al. |
| 4,787,906 A | 11/1988 | Haris |
| 4,789,663 A | 12/1988 | Wallace et al. |
| 4,789,732 A | 12/1988 | Urist |
| 4,795,804 A | 1/1989 | Urist |
| 4,804,744 A | 2/1989 | Sen |
| 4,810,691 A | 3/1989 | Seyedin et al. |
| 4,843,063 A | 6/1989 | Seyedin et al. |
| 4,902,296 A | 2/1990 | Bolander et al. |
| 5,041,138 A | 8/1991 | Vacanti et al. |
| 5,073,373 A | 12/1991 | O'Leary |
| 5,106,748 A | 4/1992 | Wozney et al. |
| 5,166,187 A | 11/1992 | Collombel et al. |
| 5,211,664 A | 5/1993 | Tepic et al. |
| 5,236,456 A | 8/1993 | O'Leary et al. |
| 5,266,683 A | 11/1993 | Oppermann et al. |
| 5,270,300 A | 12/1993 | Hunziker |
| 5,284,655 A | 2/1994 | Bogdansky et al. |
| 5,290,558 A | 3/1994 | O'Leary et al. |
| 5,290,763 A | 3/1994 | Poser et al. |
| 5,314,476 A | 5/1994 | Prewett et al. |

(Continued)

FOREIGN PATENT DOCUMENTS

DE 2 253 086 9/1974
DE 693 24 117 T2 6/1994

(Continued)

OTHER PUBLICATIONS

Landesman, Richard et al., "In Vivo Analysis of the Half-Life of the Osteoinductive Potential of Demineralized Bone Matrix Using Diffusion Chambers", *Calcif. Tissue Int.*, vol. 45, No. 6 1989, 348-353.
Laursen, Malene et al., "Optimal Handling of freshcancellous bone graft—Different peroperative storing techniques evaluated by in vitro osteobalst-like cell metabolism", *Acta Orthop Scand.*, vol. 74, No. 4 2003, 491.
Ou, Wenbin et al. "Effects of Glycerol in the Refolding and Unfolding of Creatine Kinase," *Tsinghua Science and Technology*, 7(4): 352-367 (Aug. 2002).

(Continued)

*Primary Examiner* — Allison Ford
(74) *Attorney, Agent, or Firm* — Sorell Lenna & Schmidt LLP

(57) ABSTRACT

An osteoinductive demineralized bone matrix, corresponding osteoimplants, and methods for making the osteoinductive demineralized bone matrix are disclosed. The osteoinductive demineralized bone matrix may be prepared by providing demineralized bone and altering the collagenous structure of the bone. The osteoinductive demineralized bone matrix may also be prepared by providing demineralized bone and compacting the bone, for example via mechanical compaction, grinding into a particulate, or treatment with a chemical. Additives such as growth factors or bioactive agents may be added to the osteoinductive demineralized bone matrix. The osteoinductive demineralized bone matrix may form an osteogenic osteoimplant. The osteoimplant, when implanted in a mammalian body, may induce at the locus of the implant the full developmental cascade of endochondral bone formation including vascularization, mineralization, and bone marrow differentiation. The osteoinductive demineralized bone matrix may also be used as a delivery device to administer bioactive agents.

21 Claims, 6 Drawing Sheets

(56) References Cited

U.S. PATENT DOCUMENTS

| | | | |
|---|---|---|---|
| 5,336,264 A | 8/1994 | Constanz et al. |
| 5,354,557 A | 10/1994 | Oppermann et al. |
| 5,378,469 A | 1/1995 | Kemp et al. |
| 5,385,887 A | 1/1995 | Yim et al. |
| 5,405,390 A | 4/1995 | O'Leary et al. |
| 5,490,962 A | 2/1996 | Cima et al. |
| 5,501,706 A | 3/1996 | Arenberg |
| 5,507,813 A * | 4/1996 | Dowd et al. ............. 623/23.63 |
| 5,518,680 A | 5/1996 | Cima et al. |
| 5,531,735 A | 7/1996 | Thompson |
| 5,563,124 A | 10/1996 | Damien et al. |
| 5,571,189 A | 11/1996 | Kuslich |
| 5,607,269 A | 3/1997 | Dowd et al. |
| 5,618,339 A | 4/1997 | Ito |
| 5,658,882 A | 8/1997 | Celeste et al. |
| 5,723,012 A | 3/1998 | Fages et al. |
| 5,725,579 A | 3/1998 | Fages et al. |
| 5,776,193 A | 7/1998 | Kwan et al. |
| 5,788,959 A | 8/1998 | Singh |
| 5,807,437 A | 9/1998 | Sachs et al. |
| 5,830,493 A | 11/1998 | Yokota et al. |
| 5,846,484 A | 12/1998 | Scarborough et al. |
| 5,877,005 A | 3/1999 | Castor et al. |
| 5,894,070 A | 4/1999 | Hansson et al. |
| 5,899,939 A | 5/1999 | Boyce et al. |
| 5,902,562 A | 5/1999 | Lagasse et al. |
| 5,912,131 A | 6/1999 | Eyre |
| 6,007,580 A | 12/1999 | Lehto et al. |
| 6,018,095 A | 1/2000 | Lerch et al. |
| 6,030,635 A | 2/2000 | Gertzman et al. |
| 6,117,646 A | 9/2000 | Qvist et al. |
| 6,120,558 A | 9/2000 | Poddevin et al. |
| 6,124,273 A | 9/2000 | Drohan et al. |
| 6,143,030 A | 11/2000 | Schroder |
| 6,149,864 A | 11/2000 | Dillow et al. |
| 6,162,258 A | 12/2000 | Scarborough et al. |
| 6,180,606 B1 | 1/2001 | Chen et al. |
| 6,197,325 B1 | 3/2001 | MacPhee et al. |
| 6,217,614 B1 | 4/2001 | Fages et al. |
| 6,245,537 B1 | 6/2001 | Williams et al. |
| 6,294,041 B1 | 9/2001 | Boyce et al. |
| 6,294,187 B1 | 9/2001 | Boyce et al. |
| 6,311,690 B1 | 11/2001 | Jefferies |
| 6,326,018 B1 | 12/2001 | Gertzman et al. |
| 6,352,667 B1 | 3/2002 | English |
| 6,372,257 B1 | 4/2002 | Marchosky |
| 6,387,391 B1 | 5/2002 | Shikinami et al. |
| 6,436,138 B1 | 8/2002 | Dowd et al. |
| 6,440,444 B2 | 8/2002 | Boyce et al. |
| 6,465,168 B1 | 10/2002 | Castor et al. |
| 6,468,543 B1 | 10/2002 | Gilbertson et al. |
| 6,478,825 B1 | 11/2002 | Winterbottom et al. |
| 6,592,886 B1 | 7/2003 | Zimmermann |
| 6,595,998 B2 | 7/2003 | Johnson et al. |
| 6,599,515 B1 | 7/2003 | Delmotte |
| 6,616,698 B2 | 9/2003 | Scarborough |
| 6,618,698 B1 | 9/2003 | Beausoleil et al. |
| 6,623,749 B2 | 9/2003 | Williams et al. |
| 6,648,919 B2 | 11/2003 | Ferree |
| 6,696,073 B2 | 2/2004 | Boyce et al. |
| RE38,522 E | 5/2004 | Gertzman et al. |
| 6,740,093 B2 | 5/2004 | Hochschuler et al. |
| 6,752,831 B2 | 6/2004 | Sybert et al. |
| 6,783,546 B2 | 8/2004 | Zuchermann |
| 6,843,807 B1 | 1/2005 | Boyce et al. |
| 6,884,428 B2 | 4/2005 | Binette et al. |
| 6,884,778 B2 | 4/2005 | Jo et al. |
| 6,911,212 B2 | 6/2005 | Gertzman et al. |
| 6,953,594 B2 | 10/2005 | Lee et al. |
| 6,969,404 B2 | 11/2005 | Ferree |
| 6,989,029 B2 | 1/2006 | Bonutti |
| 7,001,390 B2 | 2/2006 | Gebhardt et al. |
| 7,008,591 B2 | 3/2006 | Kafesjian et al. |
| 7,019,192 B2 | 3/2006 | Gertzman et al. |
| 7,025,771 B2 | 4/2006 | Kuslich et al. |
| 7,045,141 B2 | 5/2006 | Merboth et al. |
| 7,060,287 B1 | 6/2006 | Hubbard et al. |
| 7,108,832 B2 | 9/2006 | Christensen et al. |
| 7,163,691 B2 | 1/2007 | Knaack et al. |
| 7,179,299 B2 | 2/2007 | Edwards et al. |
| 7,208,015 B2 | 4/2007 | Pointillart et al. |
| 7,220,282 B2 | 5/2007 | Kuslich |
| 7,226,481 B2 | 6/2007 | Kuslich |
| 7,241,303 B2 | 7/2007 | Reiss et al. |
| 7,261,720 B2 | 8/2007 | Stevens et al. |
| 2001/0031254 A1 | 10/2001 | Bianchi et al. |
| 2001/0043258 A1 | 11/2001 | Ohki |
| 2002/0058947 A1 | 5/2002 | Hochschuler et al. |
| 2002/0068974 A1 | 6/2002 | Kuslich et al. |
| 2002/0077701 A1 | 6/2002 | Kuslich |
| 2002/0133166 A1 | 9/2002 | McKay et al. |
| 2002/0197297 A1 | 12/2002 | Risbud et al. |
| 2003/0008328 A1 | 1/2003 | Wironen et al. |
| 2003/0039676 A1 | 2/2003 | Boyce et al. |
| 2003/0044445 A1 | 3/2003 | Kay et al. |
| 2003/0065392 A1 | 4/2003 | Fan et al. |
| 2003/0072677 A1 | 4/2003 | Kafesjian et al. |
| 2003/0129178 A1 | 7/2003 | Wegman et al. |
| 2003/0143258 A1 | 7/2003 | Knaack et al. |
| 2003/0152548 A1 | 8/2003 | Mikos et al. |
| 2003/0194708 A1 | 10/2003 | Binnerts et al. |
| 2004/0023387 A1 | 2/2004 | Morris et al. |
| 2004/0024457 A1 | 2/2004 | Boyce et al. |
| 2004/0059364 A1 | 3/2004 | Gaskins et al. |
| 2004/0072322 A1 | 4/2004 | Thorne |
| 2004/0146543 A1 | 7/2004 | Shimp et al. |
| 2004/0220615 A1 | 11/2004 | Lin |
| 2004/0249464 A1 | 12/2004 | Bindseil et al. |
| 2005/0008620 A1 | 1/2005 | Shimp et al. |
| 2005/0008672 A1 | 1/2005 | Winterbottom et al. |
| 2005/0020506 A1 | 1/2005 | Drapeau et al. |
| 2005/0027033 A1 | 2/2005 | Knaack et al. |
| 2005/0037978 A1 | 2/2005 | Damien |
| 2005/0131417 A1 | 6/2005 | Ahern et al. |
| 2005/0244450 A1 | 11/2005 | Reddi |
| 2005/0244457 A1 | 11/2005 | Reddi |
| 2005/0251267 A1 | 11/2005 | Winterbottom et al. |
| 2005/0283255 A1 | 12/2005 | Geremakis et al. |
| 2006/0216321 A1 | 9/2006 | Lyu et al. |
| 2006/0216323 A1 | 9/2006 | Knaack et al. |
| 2006/0287732 A1 | 12/2006 | Pezeshkian |
| 2007/0073401 A1 | 3/2007 | Pointillart et al. |
| 2007/0093896 A1 | 4/2007 | Malinin |
| 2007/0098756 A1 | 5/2007 | Behnam |
| 2007/0110820 A1 | 5/2007 | Behnam |
| 2007/0118222 A1 | 5/2007 | Lang |
| 2007/0125700 A1 | 6/2007 | Ding et al. |
| 2007/0142916 A1 | 6/2007 | Olson et al. |
| 2007/0154563 A1 | 7/2007 | Behnam et al. |
| 2007/0162132 A1 | 7/2007 | Messerli |
| 2007/0178158 A1 | 8/2007 | Knaack et al. |
| 2007/0231788 A1 | 10/2007 | Behnam et al. |
| 2008/0027546 A1 | 1/2008 | Semler et al. |
| 2008/0069852 A1 | 3/2008 | Shimp et al. |
| 2008/0091270 A1 | 4/2008 | Miller et al. |
| 2008/0260794 A1 | 10/2008 | Lauritzen et al. |
| 2009/0087471 A1 | 4/2009 | Shimp et al. |
| 2009/0130173 A1 | 5/2009 | Behnam et al. |
| 2009/0157087 A1 | 6/2009 | Wei et al. |
| 2009/0192474 A1 | 7/2009 | Wei et al. |
| 2009/0220605 A1 | 9/2009 | Wei et al. |

FOREIGN PATENT DOCUMENTS

| | | |
|---|---|---|
| EP | 0 082 621 | 6/1983 |
| EP | 0 212 474 | 3/1987 |
| EP | 0 309 241 | 3/1989 |
| EP | 0 148 155 | 4/1989 |
| EP | 0 332 826 A1 | 9/1989 |
| EP | 0 440 991 | 8/1991 |
| EP | 0 567 391 A | 10/1993 |
| EP | 0 603 920 A1 | 6/1994 |
| EP | 0 621 020 A1 | 10/1994 |
| EP | 0781564 A2 | 7/1997 |

(56) References Cited

FOREIGN PATENT DOCUMENTS

| | | |
|---|---|---|
| JP | 01/179689 | 7/1989 |
| WO | WO 88/00205 | 1/1988 |
| WO | WO 88/01517 | 3/1988 |
| WO | WO 90/03733 | 4/1990 |
| WO | WO 94/21298 | 9/1994 |
| WO | WO 95/31948 | 11/1995 |
| WO | WO 96/39170 | 12/1996 |
| WO | WO 00/13615 | 3/2000 |
| WO | WO 00/45870 | 8/2000 |
| WO | WO 00/47736 | 8/2000 |
| WO | WO 01/28461 A2 | 4/2001 |
| WO | WO 01/70136 A2 | 9/2001 |
| WO | WO 01/79342 A2 | 10/2001 |
| WO | WO 02/069818 A2 | 9/2002 |
| WO | WO 03/025271 A1 | 3/2003 |
| WO | WO 03/030956 A3 | 4/2003 |
| WO | WO 2004/073563 A | 9/2004 |
| WO | WO 2005/065396 A2 | 7/2005 |
| WO | WO 2005/072656 A1 | 8/2005 |
| WO | WO 2005/081699 A2 | 9/2005 |
| WO | WO 2006/076712 | 7/2006 |
| WO | WO 2007/053850 | 5/2007 |
| WO | WO 2007/133451 | 11/2007 |

OTHER PUBLICATIONS

Ou, Wenbin et al. "Molecular Mechanism for Osmolyte Protection of Creatine Kinase Against Guanidine Denaturation," *Eur. J. Biochem.*, 268: 5901-5911 (2001).

Aspenberg et al., "Monkey Bone Matrix Induces Bone Formation in the Athymic Rat, but Not in Adult Monkeys," *J. of Orthop. Res.* 9:20-25 (1991).

Aspenberg P. et al., "Bone morphogenetic protein induces bone in the squirrel monkey, but bone matrix does not", *Acta Orthop Scand.* 63(6): 619-22 (Dec. 1992).

Blumenthal et al. "The use of collagen membrane barriers in conjunction with combined demineralized bone-collagen gel implants in human infrabony defects," *J. Periodontal* 61(6): 319-327 (Jun. 1990).

Bolander et al.,"The Use of Demineralized Bone Matrix in the Repair of Segmental Defects", *The Journal of Bone and Joint Surgery*, 68-A (8): 1264-1273, 1986.

Bravo, D.A. et al., "Accurate and Efficient Cleavage of the Human Insulin Proreceptor by the Human Proprotein-Processing Protease Furin," *Journal Biol Chem.* 269: 25830-25873 (1994).

Cameron, A. et al., "Polyarginines are potent inhibitors," *J. Biol. Chem.* 275: 36741-36749 (2000).

Canalis et al., "Bone morphogenetic proteins, their antagonists, and the skeleton," *Endocrine Rev.* 24(2): 218-235 (2003).

Canalis et al., "Stimulation of DNA and Collagen Synthesis by Autologous Growth Factor in Cultured Fetal Rat Calvaria," *Science*, 210:1021-1023 (1980).

Caplanis et al., "Effect of allogenic freeze-dried demineralized bone matrix on guided tissue regeneration in dogs," *J. Periodontal*, 851-856 (Aug. 1998).

Constantino, et al. "Bone Healing and Bone Substitutes," *Facial Plastic Surgery* 18(1): pp. 14-26 (2002).

Crowe et al., "Inhibition of Enzymatic Digestion of Amylose by Free Fatty Acids in Vitro Contributes to Resistant Starch Formation", *J. Nutr.*, 130(8): 2006-2008 (2000).

Cui et al., "The activity and signaling range of mature BMP-4 is regulated by sequential cleavage at two sites within the prodomain of the precursor," *Genes and Development*, 15:2797-2802 (2001).

Cui et al., "BMP-4 is proteolytically activated by furin and/or PC6 during vertebrae embryonic development," *The EMBO Journal*, 17(16):4735-4743 (1998).

Deatherage et al., "Packaging and Delivery of Bone Induction Factors in a Collagenous Implant," *Collagen Rel. Res.* 7:225-231 (1987).

Driessens et al., "Calcium Phosphate Bone Cements," Universitat Politecnica de Catalunya, Barcelona, Spain, 31: 855-77.

Dubois et al., "Evidence that Furin Is an Authentic Transforming Growth Facto-B-1-Converting Enxyme," *American Journal of Pathology*, 158(1):305-316 (2001).

Edwards et al., "Osteoinduction of Human Demineralized Bone: Characterization in a Rat Model," *Clinical Orthopaedics & Rel. Res.*, 357: 219-228 (Dec. 1998).

Elliott, J.C., "Structure and Chemistry of the Apatites and Other Calcium Orthophosphates", Elsevier Science B.V., Amsterdam (1994), Considered only TOC.

Enlow, Donald H., "Principles of Bone Remodeling: An Account of Post-natal Growth and remodeling Processes in Long Bones and the Mandible," Charles C. Thomas, Springfield, Ill., (1963).

Farley et al., "Human Skeletal Growth Factor: Characterization of the Mitogenic Effect on Bone Cells in Vitro," *Biochem*, 21:3508-3513 (1982).

Flemmig, et al. "Long-Term Maintenance of Alveolar Bone Gain After Implantation of Autolyzed, Antigen-Extracted, Allogenic Bone in Periodontal Intraosseous Defects," *J. Periodontal*, 69(1): 47-53 (Jan. 1998).

Fujishiro, et al. "Histological evaluation of an impacted bone graft substitute composed of a combination of mineralized and demineralized allograft in a sheep vertebral bone defect," *Journal of Biomedical Materials Research Part A*, 538-544 (Aug. 4, 2006).

Gamradt, et al. "Bone Graft for Revision Hip Arthroplasty", *Clin. Ortho. and Related Research*, 417: 183-194 (2003).

Gepstein et al. "Bridging Large Defects in Bone by Demineralized Bone Matrix in the Form of a Powder," *The Journal of Bone and Joint Surgery*, 69A(7): 984-991 (1987).

Glowacki, "Cellular Reactions to Bone-Derived Material," *Clin. Ortho. and Related Research*, 324: 47-54 (1996).

Glowacki et al., "Fate of Mineralized and Demineralized Osseous Implants in Cranial Defects," *Calcif. Tissue Int.*, 33: 71-76 (1981).

Glowacki et al., "Demineralized bone implants," *Symposium on Horizons in Plastic Surgery*, 12(2): 233-41 (1985).

Han B., et al., "Quantitive and sensitive in vitro assay for osteoinductive activity of demineralized bone matrix," *J. Orthop. Res.* 21(4): 648-54 (Jul. 2003).

Han, C. et al. "Autolysed Antigen-Extracted Allogeneic Boen for Repair of Diaphyseal Boen Defects in Rabbits," *Yonsei Medical Journal*, 31(3): 251-257 (1990).

Hollinger, et al. "A comparison of four particulate bone derivatives," *Clin. Ortho. and Related Research*, 267: 255-263 (Jun. 1991).

Hunziker et al., "Repair of Partial Thickness Defects in Articulate Cartilage: Cell Recruitment From the Synovial Membrane", *Journal Bone Joint Surg.*, 78-A: 721-733 (1996).

Iwata et al. "Chemosterilized Autolyzed Antigen-Extracted Allogeneic (AAA) Bone Matrix Gelatin for Repair of Defects from Excision of Benign Bone Tumors," *Clin. Ortho and Related Research*, 154: 150-155 (1981).

Jain et al., "Anchoring of phospholipase $A_2$: the effect of anions and deuterated water, and the role of N-terminus region," *Biochem. Et Biophys. Acta*, 860: 448-461 (1986).

Janovec, et al. "Autolyzed Antigen-Extracted Allogeneic Bone for Bridging Segmented Diaphyseal Bone Defects in Rabbits," *Clin. Ortho. and Related Research*, 229: 249-256 (Apr. 1988).

Jean et al., "Alpha 1-Antitrypsin Portland, a bioengineered serpin highly selective for furin: Application as an antipathogenic agent", *Proc. Natl. Acad. Sci.*, USA 95: 7293-7298 (1998).

Johnson et al. "Human Bone Mortphogenetic Protein Allografting for Reconstruction of Femoral Nonunion," *Clin. Ortho. and Related Research*, 371: 61-74 (2000).

Johnson et al. "Preliminary explorations of reconstructive surgery with implants of autolyzed antigen-extracted allogeneic (AAA) bone supercharged with bone morphogenetic protein (BMP)," *Bone Grafts, Derivatives and Substitutes*, published by Butterworth-Heinemann, Oxford, pp. 363-376 (1994).

Johnson et al. "Resistant Nonunions and Partial or Complete Segmental Defects of Long Bones," *Clin. Ortho. and Related Research*, 277: 229-237 (Apr. 1992).

Kaban et al., "Treatment of Jaw Defects with Demineralized Bone Implants", *Journal of Oral and Maxillofacial Surgery*, pp. 623-626 (Jun. 6, 1989).

Kasten et al., "Comparison of Human Bone Marrow Stromal Cells Seeded on Calcium-Deficient Hydroxyapatite, Betatricalcium Phosphate and Demineralized Bone Matrix", *Biomaterials*, 24(15):2593-603 (2003).

(56) References Cited

OTHER PUBLICATIONS

Katz, "The Biology of Heavy Water," *Scientific American*, 106-116 (1960).
Kawai et al., *Clin. Orthopaedics and Related Res.*, 233: 262-267 (1988).
Krysan, D.J., et al., "Quantitative Characterization of Furin Specificity", *Journal Biol. Chem.* 274, pp. 23229-23234 (1999).
Kubler et al. "Allogenic Bone & Cartilage Morphogenesis," *J. Craniomaxillofac. Surg.*, 19(7): 283-288 (1991).
Kubler et al. "Osteoinductive, morphologic, and biomechanical properties of autolyzed, antigen-extracted, allogeneic human bone," *J. Oral Maxillofac Surg*, 51: 1346-1357 (1993).
Kubler et al. "Repair of human skull defects using osteoinductive bone alloimplants," *J. of Cranio Maxillofac. Surg.* 23: 337-346 (1995).
Lee et al., *Nature*, 424: 389 (2003).
Lewandrowski et al., "Flexural Rigidity in Partially Demineralized Diaphyseal Bone Grafts", *Clin, Ortho. Rel. Res.*, 317: 254-262 (1995).
Lewandrowski et al. "Improved Osteoinduction of Cortical Bone Allografts: A Study of the Effects of Laser Perforation and Partial Demineralization" *J. Orthop. Res.* vol. 15(5): 748-756 (1997).
Lewandrowski et al. "Kinetics of cortical bone demineralization: Controlled demineralization—a new method for modifying cortical bone allografts", *Journal of Biomedical Materials Research*, vol. 31: 365-372 (1996).
Lewandrowski et al. "Mechanical Properties of Perforated and Partially Demineralized Bone Grafts," *Clin. Ortho. and Related Research*, 353: 238-246 (1998).
Lewandrowski et al., "An Electron Microscopic Study on the Process of Acid Demineralization of Cortical Bone," *Calcified Tissue Int.* 61:294-297 (1997).
Lieberman, et al. "Treatment of Osteonecrosis of the Femoral Head with Core Decompression and Human Bone Morphogenetic Protein," *Clin. Ortho. and Related Research*, 429: 139-145 (2004).
Lotz, *Clin. Orthopaedics and Related Res.*, 391S: S108-S115 (2001).
Mellonig, James. "Bone Allografts in Periodontal Therapy," *Clin. Ortho. and Related Research*, 324: 116-125 (1996).
Mellonig, "Decalcified freeze-dried bone allograft as an implant material in human periodontal defects," *The Int'l Journal of Periodontics and Restorative Dentistry*, pp. 41-45 (1984).
Miloslav et al., "Autolyzed antigen-extracted allogeneic bone for bridging segmented diaphyseal bone defects in rabbits," *Clinical Orthopaedics and Related Research*, 229: 249-256 (Apr. 1988).
Nade et al. "Decalcified Bone as a Substrate for Osteogenesis," *Bone Joint Surg.* 59(2): 189-1996 (1977).
Neigel et al. "Use of Demineralized Bone Implants in Orbital and Craniofacial Reconstruction and Review of the Literature," *Opthal. Plast. Reconst. Surg.*, 12:108 (1996).
Nogami et al., "Sustrata Prepared from Bone Matrix for Chondrogenesis in Tissue Culture", *The Journal of Cell Biology*, 62: 510-519 (1974).
Nogami et al., "Transmembrane Bone Matrix Gelatin-Induced Differentiation of Bone", *Calcif. Tiss. Res.*, 19: 153-163 (1975).
Oberg et al. "Bone formation after implantation of autolysed antigen extracted allogeneic bone in ovariectomized rabbits," *Int. J. Oral Maxillofac. Surg.* 32: 628-632 (2003).
Oberg et al. "Bone healing after implantation of hydroxyapatite granules and blocks (Interpore 200) combined with autolyzed antigen-extracted allogeneic bone and fibrin glue," *Int. J. Oral. Maxillofac. Surg.* 23: 110-114 (1994).
"Organic Reactions", vols. 1-40, John Wiley and Sons, New York, NY (1991), Considered only TOC.
Ousterhout. "Clinical Experience in Cranial and Facial Reconstruction with Demineralized Bone," *Ann. Plast. Surg.* 15(5): 367-373 (1995).
Paralkar et al., "An EP2 receptor-selective prostaglandin $E_2$ agonist induces bone healing," *PNAS*, 100(11): 6736-6740 (2003).
Peel SA et al., "In search of the ideal bone morphogenetic protein delivery system: in vitro studies on demineralized bone matrix, purified, and recombinant bone morphogenetic protein", *J. Craniofac. Surg.*, 14(3): 284-91 (May 2003).
Ray et al., "Bone Implants," *J. Bone Joint Surgery*, 39A(5): 1119-1128 (1957).
Reddi et al., "Biochemical Sequences in the Transformation of Normal Fibroblasts in Adolescent Rats," *Proc. Natl. Acad. Sci. USA*, 69(6): 1601-1605 (1972).
Ripamonti et al. "Bone induction in a composite allogeneic bone/alloplastic implant," *J. Oral Maxillofac. Surg.* 47: 963-969 (1989).
Ripamonti et al. "The induction of bone in osteogenic composites of bone matrix and porous hydroxyapatite replicas: Experimental study on the baboon," *Oral Maxillofac. Surg.* 9: 817-830 (1991).
Ripamonti. "Bone induction in nonhuman primates: an experimental study on the baboon," *Clin. Ortho. and Related Research*, 269: 284-294 (Aug. 1991).
Ripamonti. "Calvarial regeneration in primates with autolyzed antigen-extracted allogeneic bone," *Clin. Ortho. and Related Research*, 282: 293-303 (Sep. 1992).
Rodd, "Chemistry of Carbon Compounds", vols. 1-5 and supplementals, Elsevier Science Publishers, Amsterdan (1989).
Ronningen et al. "Bone formation enhanced by induction," *Acta Orthop Scan* 56: 67-71 (1985).
Ronningen et al. "Osteogenesis promoted by bone matrix combined with marrow," *Acta Orthop Scand* 5Z: 15-18 (1986).
Rosenquist et al. "Effects of bone grafting on maxillary bone healing in the growing pig," *J. Oral Maxillofac. Surg.* 40: 566-569 (1982).
Rosenthal et al. "Demineralized bone implants for nonunion fractures, bone cysts, and fibrous lesions," *Clin. Ortho. and Related Research* 362: 61-69 (1999).
Russell et al., "Clinical Utility of Demineralized Bone Matrix for Osseous Defects, Arthrodesis, and Reconstruction; Impact of Processing Techniques and Study Methodology," *Orthopaedics*, 22(5): 524-531 (May 1999).
Sailer et al. "Application of purified bone morphogenetic protein (BMP) in cranio-maxillo-facial surgery," *Jour. of Cranio-Maxillo-Facial Surgery* 22: 2-11 (1994).
Sambrook, et al. Molecular Cloning: A Laboratory Manual, $3^{rd}$ ed., Cold Spring Harbor Laboratory Press, Cold Spring Harbor (2001), Considered TOC only.
Sampath and Reddi, "Homology of bone-inductive proteins from human, monkey, bovine, and rat extracellular matrix," *Proc. Nat. Acad. Sci.* 80:6591-6594 (1983).
Sampath et al., "Bovine osteogenic protein is composed of dimmers of OP-1 and BMP-2A, Two members of the transforming growth factor-beta superfamily," *J. Biol. Chem.*, 5:265(22): pp. 13198-13205 (Aug. 1990).
Sampath et al., "Isolation of osteogenin, an extracellular matrix-associated, bone-inductive protein, by heparin affinity chromatography," *Proc. Natl. Acad. Sci.* 84(7): 7109-7113 (1987).
Schmid et al. "Osteoinduction in tibial defects in the dog," *Unfallchirurgie* 19: 1-8 (1993), Considered abstract only.
Schwarz et al., "Dog bone less osteogenetic than rat bone," *Acta. Orthop. Scan.* 60(6): 693-695 (1989).
Schwarz et al. "Decalcified and undecalcified cancellous bone block implants do not heal diaphyseal defects in dogs," *Arch. Orthop. Trauma Surg.* 111:47-50 (1991).
Serini et al., "Class 3 semaphorins control vascular morphogenesis by inhibiting integrin function," *Nature*, 424:391-397 (Jul. 2003).
Smith, Michael et al. "March's Advanced Organic Chemistry", $5^{th}$ edition, John Wiley and Sons, New York, NY (Mar. 2001), Considered only TOC.
Steadman et al., "Microfracture: Surgical Technique and Rehabilitation to Treat Chondral Defects", *Clin. Orthop.*, 391 S:362-369 (2001).
Steiner, D.F., "The proprotein convertases," *Curr. Opinion Chem. Biol.* 2: 31-39 (1998).
Temenoff et al., "Effect of poly(ethylene glycol) molecular weight on tensile and swelling properties of oligo(poly(ethylene glycol) fumarate) hydrogels for cartilage tissue engineering", *OPF Hydrogel Material Properties*, John Wiley & Sons, Inc., pp. 429-437 (2001).

(56) References Cited

OTHER PUBLICATIONS

Terashima et al., Chondrogenesis in Outgrowths of Muscle Tissue onto Modified Bone Matrix in Tissue Culture, *Clinical Orthopaedics and Related Research*, 127: 248-256 (Sep. 1977).

Todescan et al., "A Small Animal Model for Investigating Endosseous Dental Implants: Effect of Graft Materials on healing of Endoss, Porous-Surfaced Implants Placed in a Fresh Extraction Socket," *The Journal of Oral and Maxillofacial Implants*, 2(2): 217-223 (1987).

Toriumi et al. "Demineralized Bone," Arch Otolaryngol Head Neck Surg. 116: 676-680 (Jun. 1990).

Ueland et al., *J. Clin. Endocrinol. & Metab.*, 84(1): 123-127 (1999).

Urist. "Bone: Formation by Autoinduction," *Science*, 150(698): pp. 893-899 (1965).

Urist. "The Bone Induction Principle," *Clin. Ortho. Rel. Res.*, 55: 243-283 (1967).

Urist et al., "Bone morphogenesis in Implants of Insoluble Bone Gelatin," *Proc. Natl. Acad. Sci.*, , 70(12): 3511-5 (Dec. 1973).

Urist et al., ., "Preservation and biodegradation of the morphogenetic property of bone matrix," *J. Theor. Biol.* 38: 155-67 (1973).

Urist et al., "Observations implicating an extracellular enzymic mechanism of control of bone morphogenesis," *J. Histochem & Cytochem*, 22(2): 88-103 (1974).

Urist et al., "A Chemosterilized Antigen-Extracted Autodigested Alloimplant for Bone Banks," *Arch Surg.* vol. 110: 416-428 (Apr. 1975).

Urist et al., "Cartilage Tissue Differentiation from Mesenchymal Cells Derived from Mature Muscle in Tissue Culture", *In Vitro*, 14(8): 697-706 (1978).

Urist et al. "Intertransverse Process Fusion with the Aid of Chemosterilized Autolyzed Antigen-Extracted Allogeneic (AAA) Bone," *Clin. Ortho. and Related Research*, 154: 97-113 (1981).

Urist et al., "Human Bone Morphogenetic Protein (hBMP)," *Proc. Soc. Exp. Biol.* 173:194-199 (1983).

Urist et al., "Purification of bovine bone morphogenetic protein by hydroxyapatite chromatography," *Prop. Natl. Acad. Sci.* 81:371-375 (1984).

Van den Berg et al., "Tissue Engineering, Cells, Scaffolds, and Growth Factors," *Clin. Orthopaedics and Related Res.*, 391S: S244-S250 (2001).

Van den Ouweland, A.M.W. et al., "Structural homology between the human *fur* gene product and the subtilisin-like protease encoded by yeast *KEX2*," *Nucl. Acid Res.* 18(3): 664 (1990).

Wang et al., "Purification and characterization of other distinct bone-inducing factors," *Proc. Nat. Acad. Sci.* 85:9484-9488 (1988).

Wang et al., "Recombinant human bone morphogenetic protein induces bone formation," *Proc. Nat. Acad. Sci.* 87:2220-2224 (1990).

White et al., "Effective terminal sterilization using supercritical carbon dioxide," *Journal of Biotechnology*, 123: 504-515 (2006).

Whiteman et al., "Demineralized Bone Powder," *J. Hand. Surg.*, 18B(4): 487-90 (1993).

Whittaker et al., "Matrix Metalloproteinases and Their Inhibitors—Current Status and Future Challenges," *Celltransmissions*, 17(1): 3-14.

Wise, D.L., "Encyclopedia Handbook of Biomaterials and Bioengineering Part B", Applications New York: Marcel Decker (1995), Considered TOC only.

Xiaobo et al., "Experimental and Clinical Investigations of Human Insoluble Bone Matrix Gelatin," *Clin. Orthopaedics and Related Research*, 293: 360-365 (1993).

Young et al. "Morphological changes of autoclaved autogenic bone implantation and autoclaved autogenic bone supplemented with allogenic demineralized bone matrix in rat parietal bone," *Histol Histopathol.* 11: 361-369 (1996).

Zhang et al., "A Quantitative assessment of osteoinductivity of human demineralized bone matrix," *J. Periodontal*, 68(11): 1076-84 (Nov. 1997).

\* cited by examiner

200

OSTEOINDUCTIVE DEMINERALIZED CANCELLOUS BONE

This application claims benefit of U.S. Ser. No. 60/944,417, filed on Jun. 15, 2007 and U.S. Ser. No. 60/986,843 filed on Nov. 9, 2007, each of which are hereby incorporated by reference in their entireties.

BACKGROUND

Introduction

Mammalian bone tissue is known to contain one or more proteinaceous materials, presumably active during growth and natural bone healing, that can induce a developmental cascade of cellular events resulting in endochondral bone formation. The active factors variously have been referred to in the literature as bone morphogenetic or morphogenic proteins (BMPs), bone inductive proteins, bone growth or growth factors, osteogenic proteins, or osteoinductive proteins. These active factors are collectively referred to herein as osteoinductive factors.

It is well known that bone contains these osteoinductive factors. These osteoinductive factors are present within the compound structure of cortical bone and are present at very low concentrations, e.g., 0.003%. Osteoinductive factors direct the differentiation of pluripotential mesenchymal cells into osteoprogenitor cells that form osteoblasts. Based upon the work of Marshall Urist as shown in U.S. Pat. No. 4,294,753, issued Oct. 13, 1981, proper demineralization of cortical bone exposes the osteoinductive factors, rendering it osteoinductive, as discussed more fully below.

Overview of Bone Grafts

The rapid and effective repair of bone defects caused by injury, disease, wounds, or surgery has long been a goal of orthopaedic surgery. Toward this end, a number of compositions and materials have been used or proposed for use in the repair of bone defects. The biological, physical, and mechanical properties of the compositions and materials are among the major factors influencing their suitability and performance in various orthopaedic applications.

Autologous cancellous bone ("ACB") long has been considered the gold standard for bone grafts. ACB is osteoinductive and nonimmunogenic, and, by definition, it has all of the appropriate structural and functional characteristics appropriate for the particular recipient. Unfortunately, ACB is only available in a limited number of circumstances. Some individuals lack ACB of appropriate dimensions and quality for transplantation, and donor site pain and morbidity can pose serious problems for patients and their physicians.

Much effort has been invested in the identification and development of alternative bone graft materials. Urist has published seminal articles on the theory of bone induction and a method for decalcifying bone, i.e., making demineralized bone matrix (DBM). Urist M. R., *Bone Formation by Autoinduction,* 150 Science 698, 893-899 (1965); Urist M. R. et al., *The Bone Induction Principle,* 53 Clin. Orthop. Rel. Res. 243-283 (1967). As mentioned above, it is known that DBM that is derived from cortical bone is an osteoinductive material, in that it induces bone growth when implanted in an ectopic site of a rodent, owing to the osteoinductive factors contained within the DBM. It is also known that there are numerous osteoinductive factors, e.g., BMP 1-15, which are part of the transforming growth factor-beta (TGF-beta) superfamily BMP-2 has become the most important and widely studied of the BMP family of proteins. There are also other proteins present in DBM that are not osteoinductive alone but still contribute to bone growth, including fibroblast growth factor-2 (FGF-2), insulin-like growth factor-I and -II (IGF-I and IGF-II), platelet derived growth factor (PDGF), and transforming growth factor-beta 1 (TGF-beta. 1).

DBM implants have been reported to be particularly useful (see, for example, U.S. Pat. Nos. 4,394,370, 4,440,750, 4,485,097, 4,678,470, and 4,743,259; Mulliken et al., Calcif Tissue Int. 33:71, 1981; Neigel et al., Opthal. Plast. Reconstr. Surg. 12:108, 1996; Whiteman et al., J. Hand. Surg. 18B:487, 1993; Xiaobo et al., Clin. Orthop. 293:360, 1993, each of which is incorporated herein by reference). DBM typically is derived from cadavers. The bone is removed aseptically and treated to kill any infectious agents. The bone is particulated by milling or grinding, and then the mineral component is extracted by various methods, such as by soaking the bone in an acidic solution. The remaining matrix is malleable and can be further processed and/or formed and shaped for implantation into a particular site in the recipient. Demineralized bone prepared in this manner contains a variety of components including proteins, glycoproteins, growth factors, and proteoglycans. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient.

It is generally accepted that cancellous demineralized bone matrix does not have osteoinductive capacity. One study found that allogeneic cancellous bone blocks, demineralized or not, have no osteoinductive capacity and no osteoconductive function that promotes healing of mid-diaphyseal bone defects in dogs. Schwarz et al., Arch Orthop Trauma Surg., 1991; 111(1):47-50; see also Nade et al., J Bone Joint Surg Br 1997 May 59(2):189-96.

Some studies indicate that the osteoinductive capabilities of demineralized bone from higher order species in higher order species is relatively low. One study compared the osteoinductivity of rat and canine bone matrix. The study looked at rat cortical bone matrix, canine cortical bone matrix, and canine cancellous bone matrix. Cortical rat bone matrix consistently induced new bone and high phosphatase levels when implanted ectopically in rat. Canine matrix induced small amounts of bone and lower phosphatase levels when implanted in dog and in rat, with cortical matrix being somewhat more inductive than cancellous matrix. Demineralized cancellous bone matrix from dog was the only material tested not showing any osteoinductivity. Schwarz et al., Acta. Orthop. Scan. 60(6):693-695, 1989.

Another study, looking at cortical bone matrix from monkeys, determined that monkey bone matrix induces ectopic bone formation in the athymic rat but not in adult monkeys. It was concluded that adult monkey bone matrix contains bone inductive properties but that these properties are not sufficient to induce bone formation in adult monkey muscle sites. Aspenberg et al., J. of Orthop. Res. 9:20-25, 1991.

Yet another study evaluated bone and cementum regeneration following guided tissue regeneration (GTR) in periodontal fenestration defects. Specifically, the adjunctive effect of allogenic, freeze-dried DBM implant was evaluated and found to exhibit no discernible adjunctive effect to GTR in the defect model. The critical findings were 1) the DBM particles remained embedded in dense connective tissue without evidence of bone metabolic activity; and 2) limited and similar amounts of bone and cementum regeneration were observed for GTR plus DBM and GTR defects. Caplanis et al., J Periodontal 851-856, August, 1998.

Current DBM formulations have various drawbacks. First, while the collagen-based matrix of DBM is relatively stable, the osteoinductive factors within the DBM matrix are rapidly degraded. The osteogenic activity of the DBM may be significantly degraded within 24 hours after implantation, and in some instances, the osteogenic activity may be inactivated within 6 hours. Therefore, the osteoinductive factors associated with the DBM are only available to recruit cells to the site of injury for a short time after transplantation. For much of the healing process, which may take weeks to months, the implanted material may provide little or no assistance in recruiting cells. In addition to the osteoinductive factors present within the DBM, the overall structure of the DBM implant is also believed to contribute to the bone healing capabilities of the implant.

U.S. Pat. No. 4,563,350, herein incorporated by reference in its entirety, discloses the use of trypsinized bovine bone matrix as a xenogenic matrix to effect osteogenic activity when implanted with extracted, partially purified bone-inducing protein preparations. Bone formation is said to require the presence of at least 5%, and preferably at least 10%, non-fibrillar collagen. The named inventors claim that removal of telopeptides that are responsible in part for the immunogenicity of collagen preparations is more suitable for xenogenic implants.

European Patent Application Serial No. 309,241, published Mar. 29, 1989, herein incorporated by reference in its entirety, discloses a device for inducing endochondral bone formation comprising an osteogenic protein preparation, and a matrix carrier comprising 60-98% of either mineral component or bone collagen powder and 2-40% atelopeptide hypoimmunogenic collagen.

U.S. Pat. No. 3,394,370, herein incorporated by reference in its entirety, describes a matrix of reconstituted collagen purportedly useful in xenogenic implants. The collagen fibers are treated enzymatically to remove potentially immunogenic telopeptides (also the primary source of interfibril crosslinks), and are dissolved to remove associated noncollagenenous components. The matrix is formulated by dispersing the reconstituted collagen in acetic acid to form a disordered matrix of elementary collagen molecules that is then mixed with an osteogenic substance and lyophilized to form a "semi-rigid foam or sponge" that is preferably crosslinked.

U.S. Pat. No. 4,172,128, herein incorporated by reference in its entirety, describes a method for degrading and regenerating bone-like material of reduced immunogenicity, said to be useful cross-species. Demineralized bone particles are treated with a swelling agent to dissolve any associated mucopolysaccharides (glycosaminoglycans), and the collagen fibers subsequently dissolved to form a homogenous colloidal solution. A gel of reconstituted fibers then can be formed using physiologically inert mucopolysaccharides and an electrolyte to aid in fibril formation.

Various papers have looked at cartilage tissue differentiation of bone matrix gelatin (BMG) from cortical bone. Terashima and Urist found that cortical bone BMG is chemically more reactive than whole bone matrix. Terashima et al., *Chondrogenesis in Outgrowths of Muscle Tissue onto Modified Bone Matrix in Tissue Culture*, 127 Clin. Orthop. and Rel. Res. 248-256 (1977). A later study found that rat BMG may induce chondrogenesis in cell culture. Urist et al., *Cartilage Tissue Differentiation from Mesenchymal Cells Derived from Mature Muscle in Tissue Culture*, 14(8) In Vitro 697-706 (1978). Nogami and Urist also assessed the effect of various treatments of cortical bone, including collagenase treatment of cortical bone BMG, on cartilage tissue differentiation. Nogami and Urist, *Substrata Prepared from Bone Matrix for Chondrogenesis in Tissue Culture*, 62 J. of Cell Bio. 510-519 (1974).

A variety of approaches have been explored in an attempt to recruit progenitor cells or chondrocytes into an osteochondral or chondral defect. For example, penetration of subchondral bone has been performed in order to access mesenchymal stem cells (MSCs) in the bone marrow, which have the potential to differentiate into cartilage and bone. Steadman, et al., *Microfracture: Surgical Technique and Rehabilitation to Treat Chondral Defects* 391 S Clin. Orthop. 362-369 (2001). In addition, some factors in the body are believed to aid in the repair of cartilage. For example, transforming growth factors beta (TGF-β) have the capacity to recruit progenitor cells into a chondral defect from the synovium or elsewhere when loaded in the defect. Hunziker, et al., *Repair of Partial Thickness Defects in Articular Cartilage: Cell Recruitment From the Synovial Membrane*, 78-A J. Bone Joint Surg., 721-733 (1996). However, the application of growth factors to bone and cartilage implants has not resulted in the expected increase in osteoinductive or chondrogenic activity.

Each of U.S. Pat. Nos. 5,270,300 and 5,041,138, each herein incorporated by reference in its entirety, describes a method for treating defects or lesions in cartilage that provides a matrix, possibly composed of collagen, with pores large enough to allow cell population and contain growth factors (TGF-β or other factors (such as angiogenesis factors)) appropriate for the type of tissue desired to be regenerated.

BRIEF SUMMARY

Osteoinductive compositions, and implants and methods for their production, are provided. At least partially demineralized bone matrix is treated to enhance the osteoinductive activity of the bone matrix. More specifically, the at least partially demineralized bone matrix may be treated with enzymes, chemicals, ionizing radiation, electromagnetic radiation, compaction, or other treatments to impart or enhance osteoinductive activity of the bone matrix.

This application refers to various patents, patent applications, journal articles, and other publications, all of which are incorporated herein by reference in their entireties. The following documents are incorporated herein by reference in their entireties: PCT Publications PCT/US04/43999 and PCT/US05/003092; US Patent Application Pub. No. 2003/0143258 A1; PCT Publication PCT/US02/32941; Current Protocols in Molecular Biology, Current Protocols in Immunology, Current Protocols in Protein Science, and Current Protocols in Cell Biology (John Wiley & Sons 2002); Sambrook, Russell, and Sambrook, Molecular Cloning: A Laboratory Manual, (Cold Spring Harbor Laboratory Press 2001); Rodd, Chemistry of Carbon Compounds, vols. 1-5 and supps. (Elsevier Science Publishers 1989); Organic Reactions, vols. 1-40 (John Wiley & Sons 1991); Advanced Organic Chemistry, (John Wiley & Sons 2001). In the event of a conflict between the specification and any of the incorporated references, the specification shall control.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

DEFINITIONS

Figure 1:
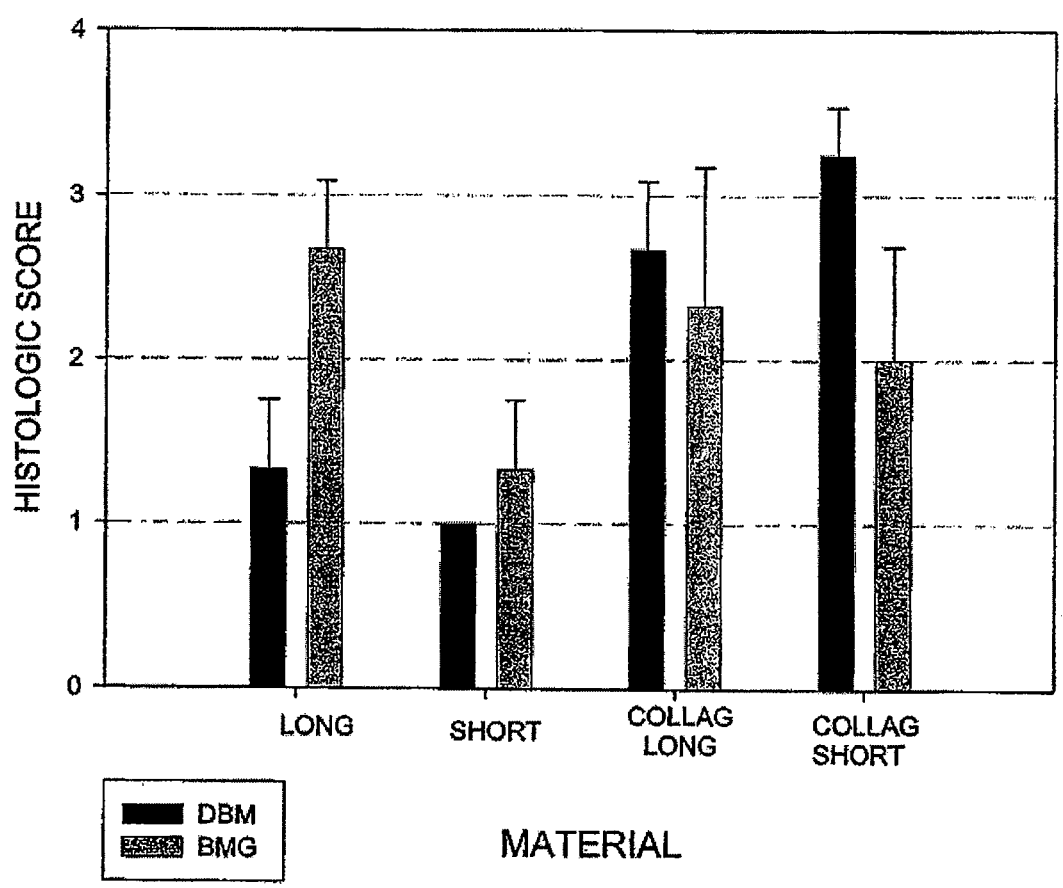
FIG. 1 illustrates the results of Example 1.

Bioactive Agent or Bioactive Compound, as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present invention may be found in Axel Kleemann and Jurgen Engel, Pharmaceutical Substances Syntheses, Patents, Applications (Thieme Medical Publishing 1999); the Merck Index: An Encyclopedia of Chemicals, Drugs, and Biologicals (Susan Budavari et al., CRC Press 1996); and the United States Pharmacopeia-25/National Formulary-20 (United States Pharmcopeial Convention, Inc. 2001), each of which is incorporated herein by reference in their entireties.

Biocompatible, as used herein, refers to materials that, upon administration in vivo, do not induce undesirable long-term effects.

Bone, as used herein, refers to bone that is cortical, cancellous or cortico-cancellous of autogenous, allogenic, xenogenic, or transgenic origin.

Demineralized, as used herein, refers to material generated by removing mineral material from tissue, e.g., bone tissue. In certain embodiments, demineralized compositions as described herein may include preparations containing less than 5% calcium, or less than 1% calcium by weight. Partially demineralized bone is intended to refer to preparations with greater than 5% calcium by weight but containing less than 100% of the original starting amount of calcium. In some embodiments, demineralized bone has less than 95% of its original mineral content. Percentage of demineralization may refer to percentage demineralized by weight, or to percentage demineralized by depth, as described with reference to FIGS. 4a and 4b. Surface demineralized bone is a subset of partially demineralized bone and refers to compositions having a demineralized surface and a non-demineralized core. Superficially demineralized refers to bone-derived elements possessing at least about 90 percent of their original inorganic mineral content. Partially demineralized refers to bone-derived elements possessing from about 8 to about 90 percent of their original inorganic mineral content. Fully demineralized refers to bone containing less than 8% of its original mineral context. Demineralized bone encompasses such expressions as "substantially demineralized," "partially demineralized," "surface demineralized," and "fully demineralized."

Osteoconductive, as used herein, refers to the ability of a non-osteoinductive substance to serve as a suitable template or substance along which bone may grow.

Osteogenic, as used herein, refers to the ability of an agent, material, or implant to enhance or accelerate the growth of new bone tissue by one or more mechanisms such as osteogenesis, osteoconduction, and/or osteoinduction.

Osteoimplant, as used herein, refers to any bone-derived implant prepared in accordance with the embodiments of this invention and therefore is intended to include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., *Osteoinduction of Human Demineralized Bone: Characterization in a Rat Model,* 357 Clinical Orthopaedics & Rel. Res. 219-228 (1998), incorporated herein by reference in its entirety. In other instances, osteoinduction is considered to occur through cellular recruitment and induction of the recruited cells to an osteogenic phenotype. Osteoinductivity score refers to a score ranging from 0 to 4 as determined according to the method of Edwards et al., *Osteoinduction of Human Demineralized Bone: Characterization in a Rat Model,* 357 Clinical Orthopaedics & Rel. Res. 219-228 (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally osteoinductivity also may be scored at later timepoints such as 40, 60, or even 100 days following implantation. Percentage of osteoinductivity refers to an osteoinductivity score at a given time point, expressed as a percentage of activity, of a specified reference score.

Proteases, as used herein, refers to protein-cleaving enzymes that cleave peptide bonds that link amino acids in protein molecules to generate peptides and protein fragments. A large collection of proteases and protease families has been identified. Some exemplary proteases include serine proteases, aspartyl proteases, acid proteases, alkaline proteases, metalloproteases, carboxypeptidase, aminopeptidase, cysteine protease, collagenase, etc. An exemplary family of proteases is the proprotein convertase family, which includes furin. Dubois et al., 158(1) Am. J. of Pathology 305-316 (2001). Members of the proprotein convertase family of proteases are known to proteolytically process proTGFs and proBMPs to their active mature forms. Dubois et al., 158(1) Am. J. of Pathology 305-316 (2001); Cui et al., 17(16) Embo J. 4735-4743 (1998); Cui et al., 15 Genes & Development 2797-2802 (2001), each incorporated by reference herein in their entireties.

Protease inhibitors, as used herein, refers to chemical compounds capable of inhibiting the enzymatic activity of protein cleaving enzymes (i.e., proteases). The proteases inhibited by these compounds include serine proteases, acid proteases, metalloproteases, carboxypeptidase, aminopeptidase, cysteine protease, etc. The protease inhibitor may act specifically to inhibit only a specific protease or class of proteases, or it may act more generally by inhibiting most if not all proteases. Some protease inhibitors are protein- or peptide-based and are commercially available from chemical companies such as Aldrich-Sigma. Protein or peptide-based inhibitors adhere to the DBM (or calcium phosphate or ceramic carrier) may provide particular benefits as they remain associated with the matrix providing a stabilizing effect for a longer period of time than freely diffusible inhibitors. Examples of protease inhibitors include aprotinin, 4-(2-aminoethyl) benzenesulfonyl fluoride (AEBSF), amastatin-HCl, alpha1-antichymotrypsin, antithrombin III, alpha1-antitrypsin, 4-aminophenyl-methane sulfonyl-fluoride (APMSF), arphamenine A, arphamenine B, E-64, bestatin, CA-074, CA-074-Me, calpain inhibitor I, calpain inhibitor II, cathepsin inhibitor, chymostatin, diisopropylfluorophosphate (DFP), dipeptidylpeptidase IV inhibitor, diprotin A, E-64c, E-64d, E-64, ebelactone A, ebelactone B, EGTA, elastatinal, foroxymithine, hirudin, leuhistin, leupeptin, alpha2macroglobulin, phenylmethylsulfonyl fluo4de (PMSF), pepstatin A, phebestin, 1,10 phenanthroline, phosphoramidon, chymostatin, benzamidine HCl, antipain, epsilon aminocaproic acid, N-ethylmaleimide, trypsin inhibitor, 1-chloro-3-tosylamido-7-amino-2-heptanone (TLCK), 1-chloro-3-tosylamido-4-phenyl-2-butanone (TPCK), trypsin inhibitor, and sodium EDTA.

Stabilizing agent, as used herein, refers to any chemical entity that, when included in an inventive composition comprising DBM and/or a growth factor, enhances the osteoinductivity of the composition as measured against a specified reference sample. In most cases, the reference sample will not contain the stabilizing agent, but in all other respects will be the same as the composition with stabilizing agent. The stabilizing agent also generally has little or no osteoinductivity of its own and works either by increasing the half-life of one or more of the active entities within the inventive composition as compared with an otherwise identical composition lacking the stabilizing agent, or by prolonging or delaying the release of an active factor. In certain embodiments, the stabilizing agent may act by providing a barrier between proteases and sugar-degrading enzymes thereby protecting the osteoinductive factors found in or on the matrix from degradation and/or release. In other embodiments, the stabilizing agent may be a chemical compound that inhibits the activity of proteases or sugar-degrading enzymes. According to certain embodiments, the stabilizing agent retards the access of enzymes known to release and solubilize the active factors. Half-life may be determined by immunological or enzymatic assay of a specific factor, either as attached to the matrix or extracted therefrom. Alternatively, measurement of an increase in osteoinductivity half-life, or measurement of the enhanced appearance of products of the osteoinductive process (e.g., bone, cartilage or osteogenic cells, products or indicators thereof), is a useful indicator of stabilizing effects for an enhanced osteoinductive matrix composition. The measurement of prolonged or delayed appearance of a strong osteoinductive response will generally be indicative of an increase in stability of a factor coupled with a delayed unmasking of the factor activity.

DETAILED DESCRIPTION

I. Introduction

Osteoinductive compositions and implants and methods for their production are provided. According to certain embodiments, at least partially demineralized bone is treated with one or more enzymes, chemicals, ionizing radiation, electromagnetic radiation, or compaction to impart or enhance osteoinductive activity of the bone. The bone may be cancellous, corticocancellous, cortical, or a composite bone. The bone may be fully demineralized, partially demineralized, or surface demineralized. In some embodiments, the bone is particulated, such as through grinding, and the particles are compacted. Those of ordinary skill will appreciate that a variety of embodiments or versions of the invention are not specifically discussed below but are nonetheless within the scope of the present invention, as defined by the appended claims.

Bone is made up principally of cells, and also of collagen, minerals, and other noncollagenous proteins. Cortical bone accounts for approximately eighty percent of skeletal bone mass. Cortical bone is structural and bears the majority of the body's weight. Cancellous bone is relatively porous and spongy and accounts for approximately twenty percent of skeletal bone mass. Cancellous bone contains bone marrow and elements required for bone to heal itself. The physical characteristics of cancellous bone make it an ideal material for a variety of orthopaedic applications including spinal fusions, maxillofacial and craniofacial reconstruction, and treatment of long bone defects. Despite desirable physical characteristics, cancellous bone may not be used in some applications because it is generally accepted that cancellous demineralized bone has minimal or no osteoinductive capacity.

Bone is living, growing tissue. In vivo, bone is constantly being renewed. The old bone is removed and new bone is laid down. There are two phases, involving cellular activities, in this process. The first phase, removal of old bone, is osteoclastic resorption. Osteoclasts dissolve some tissue on the surface of the bone and create a small cavity. Typically this process takes place over a few days. The second phase, laying down of new bone, is osteoblastic formation. Osteoblasts fill the cavities created by the osteoclasts with new bone. Typically this process takes a few months. Factors such as hormones, calcium, exercise, and other can affect the cells on the surface of bone and trigger the remodeling cycle.

An osteoinductive bone matrix is provided by altering the natural collagenous structure of the bone. In some embodiments, the osteoinductive bone matrix is an osteoinductive cancellous bone matrix, thus providing a graft material with desirable physical characteristics and osteoinductive capacity. In one embodiment, this is done by altering the collagenous structure of the bone such that the structure may be at least partially resorbed. In another embodiment, this is done by compacting the trabecular structure of the bone. In vivo, the osteoinductive bone matrix triggers the remodeling cycle.

It is to be appreciate that, while the description herein may refer to cancellous bone for illustrative purposes, one skilled in the art would appreciate that the discussion may be applied to cortical, corticocancellous, or composite bone.

II. Overview of Increasing the Osteoinductive Potential of Bone Matrix

Methods for increasing the biological activity of an at least partially demineralized bone matrix are provided. Osteoinductive osteoimplants are further provided. The osteoinductive osteoimplants comprise at least partially demineralized bone having increased biological activity relative to at least partially demineralized bone that has not been exposed to a treatment or condition as described herein. In some embodiments, the osteoinductive osteoimplants may comprise at least partially demineralized cancellous bone that has been exposed to a treatment or condition as described herein. The biological activities that may be increased include but are not limited to osteoinductive activity, osteogenic activity, chondrogenic activity, triggering of bone remodeling, wound healing activity, neurogenic activity, contraction-inducing activity, mitosis-inducing activity, differentiation-inducing activity, chemotactic activity, angiogenic or vasculogenic activity, and exocytosis- or endocytosis-inducing activity. U.S. patent application Ser. No. 12/140,044 to Bone Matrix Compositions and Methods, filed Jun. 16, 2008, is herein incorporated by reference in its entirety for the purposes of all that is disclosed therein. It will be appreciated that bone formation processes frequently include a first stage of cartilage formation that creates the basic shape of the bone, which then becomes mineralized (endochondral bone formation). Thus, in many instances, chondrogenesis may be considered an early stage of osteogenesis, though of course it may also occur in other contexts.

The at least partially demineralized bone, including wherein the at least partially demineralized bone is at least partially demineralized cancellous bone, provided herein exhibits osteoinductive activity. The osteoinductive at least partially demineralized bone may be prepared by providing at least partially demineralized bone and altering the collagenous structure of the at least partially demineralized bone. Generally speaking, the osteoinductivity of the at least partially demineralized bone may be increased by either (1) altering the structure of the bone such that the trabecular density is increased while the collagen structure is decreased, or (2) by opening up the structure of the bone, thus breaking the collagen apart and making growth factors within the bone more accessible. Thus, in certain embodiments, the at least partially demineralized bone is exposed to a biological or chemical agent or to a combination of agents. The agent may be a cleavage agent, e.g., a protease such as collagenase(s), or a chemical agent such as cyanogen bromide. The matrix may be exposed to multiple treatments either together or sequentially. While not wishing to be bound by any theory, the treatment may alter the primary, secondary, tertiary, and/or quaternary structure of a component of the bone matrix (e.g., collagen, a bone morphogenetic protein, etc.) so as to increase the biological activity of the matrix. An inventive treatment or condition may "open up" the structure of the matrix, e.g., so as to allow biologically active molecules to be more readily released from or diffuse within the matrix and/or to allow components such as nutrients or growth-stimulatory molecules to enter the matrix. In certain embodiments the treatment or condition cleaves proteins present in the DBM (e.g., proteins such as bone morphogenetic proteins), which may result in conversion of an inactive protein into an active form, and/or may generate an active molecule that is less susceptible to degradation than a longer molecule from which it is derived. In certain embodiments, the bone is ground to a generally powder consistency and the powder is reaggregated into a dense structure through compression.

In certain embodiments, it is thought that the at least partially demineralized bone provided herein triggers the remodeling cycle. Specifically, remodeling of bone may be directed to sites that show damage such as microcracks. It is theorized that the body recognizes tissue regions that need repair and then sends cells to repair those regions. Thus, by treating or damaging the at least partially demineralized bone by, for example, treating or damaging the collagen, the at least partially demineralized bone is "marked" as requiring repair. Thus, an implant formed from the cancellous at least partially demineralized bone is marked as requiring repair by cells. In some embodiments, inductive materials may be added to the implant to further stimulate bone remodeling. Alternatively, or additionally, native inductive materials in the bone may be exposed. The bone may be compacted to concentrate the inductive materials (added or native). The implant exhibiting tissue damage and, in some embodiments, increased and/or concentrated inductive material triggers a rapid biologic response.

The treatment or condition may cleave an inhibitory factor that would otherwise inhibit a positively acting agent (an agent that enhances a biological activity of the bone matrix). For example, a variety of proteins or protein fragments are known to inhibit the osteoinductive and/or osteogenic activity of certain bone morphogenetic proteins, such as BMP-2. In certain embodiments of the invention, the inhibitory effect of a protein or protein fragment may be reduced by exposing a bone or cartilage matrix to a treatment or condition. The treatment or condition may cause the cleavage or degradation of the inhibitory agent. The treatment or condition may block the interaction of the inhibitory agent with its target (e.g., BMP-2) or may inhibit synthesis, secretion, post-translational modification, transport, etc. of the inhibitory agent. For example, the bone matrix may be exposed to cleave antibody inhibitory agents, or the antibody may be added to the bone matrix.

The osteoinductive at least partially demineralized bone may form an osteogenic and osteoinductive osteoimplant, discussed more fully below. In embodiments wherein the at least partially demineralized bone is at least partially demineralized cancellous bone, the osteoimplant may have desirable characteristics of cancellous bone and yet also have osteoinductive capacity. The osteoimplant, when implanted in a mammalian body, may induce, at the locus of the implant, the full developmental cascade of endochondral bone formation including vascularization, mineralization, and bone marrow differentiation. Also, in some embodiments, the osteoinductive at least partially demineralized bone may be used as a delivery device to administer bioactive agents.

Altering the Structure of the at Least Partially Demineralized Bone

In one embodiment, the collagenous structure of the at least partially demineralized bone is disrupted such that the demineralized bone may be at least partially resorbed after implantation. For example, at least partially demineralized bone may be altered so that it has a solid structure at room temperature but substantially liquefies in the body or in tissue culture media such that it may have increased osteoinductive activity when compared to standard at least partially demineralized bone.

Cancellous femoral bone has been shown to contain osteoinductive growth factors that may be extracted from human bone. In one embodiment, cancellous DBM may be treated with, for example, collagenase, which is believed to open the structure of the cancellous DBM to make the growth factors within the bone more bioaccessible. After treatment with collagenase, the osteoinductive cancellous DBM may substantially liquefy in the body and may be at least partially resorbed by the body when implanted.

Compacting the Structure

Cortical bone includes dense lamellar structure. The structure of cancellous bone is less dense than that of the lamellar structure of cortical bone. If demineralized bone is considered to be a growth factor source, the growth factor concentration gradients produced by implantation of cancellous and cortical allograft may differ significantly. By compressing the structure of cancellous bone, the osteoinductive potential may be increased. In some embodiments, the structure of cortical bone may be compacted.

Compression of the at least partially demineralized bone may be achieved via any suitable mechanism. For example, compression may be achieved by mechanical means, heat, chemical modification of the bone structure, any suitable type of compression processing, or combinations of these. In one embodiment, the bone is ground or otherwise processed into particles of an appropriate size and formed into a dense bone structure. Grinding may produce bone of a powder like consistency, the powder is wet, and the wet bone powder is smeared to a consistency of fibrous paste. The fibrous paste may be compressed and the paste may be permitted to dry. It is to be appreciated that the bone may be particulated before or after demineralization. Thus, for example, the bone may be particulated and thereafter partially demineralized. Alternatively, the bone may be demineralized and then particulated.

In some embodiments, the bone may be compressed by loading cancellous bone in constrained compression, for example via palletizing the bone, without grinding the bone. Thus, in various embodiments, the at least partially demineralized bone is mechanically compacted into a dense structure. In yet other embodiments, the at least partially demineralized bone is compacted by treatment with chemicals, such as lithium chloride (LiCl), thereby shrinking the collagenous structure.

III. Providing Demineralized Bone

In some embodiments, demineralized bone that is substantially fully demineralized is used. In other embodiments, partially demineralized bone is used. In other embodiments, the surface demineralized bone is used. In other embodiments, nondemineralized bone may be used. In other embodiments, combinations of some of all of the above may be used. While many of the examples in this section refer to partially or surface demineralized bone, this is for illustrative purposes.

In one embodiment, the bone is partially demineralized. The at least partially demineralized bone may be provided in any suitable manner. The bone useful in the invention herein is obtained utilizing methods well known in the art, e.g., allogenic donor bone. Bone-derived elements may be readily obtained from donor bone by various suitable methods, e.g., as described in U.S. Pat. No. 6,616,698, incorporated herein by reference in its entirety. The bone may be of autogenous, allogenic, xenogenic, or transgenic origin.

DBM preparations have been used for many years in orthopaedic medicine to promote the formation of bone. Typically, DBM preparations for promoting the formation of bone have comprised cortical or corticocancellous DBM. DBM has found use, for example, in the repair of fractures, in the fusion of vertebrae, in joint replacement surgery, and in treating bone destruction due to underlying disease such as rheumatoid arthritis. Cortical DBM is thought to promote bone formation in vivo by osteoconductive and osteoinductive processes. The osteoinductive effect of implanted cortical DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There also are likely to be other unnamed or undiscovered osteoinductive factors present in DBM. Cancellous DBM is understood to have little or no osteoinductive capacity.

In one demineralization procedure of the present invention, the bone is subjected to an acid demineralization step and a defatting/disinfecting step. The bone is immersed in acid over time to effect demineralization. Acids that may be employed in this step include inorganic acids such as hydrochloric acid and as well as organic acids such as formic acid, acetic acid, peracetic acid, citric acid, propionic acid, etc. Demineralization may be to a point where the bone is fully demineralized, partially demineralized, or surface demineralized. The depth of demineralization into the bone surface may be controlled by adjusting the treatment time, temperature of the demineralizing solution, concentration of the demineralizing solution, and agitation intensity during treatment.

The at least partially demineralized bone is rinsed with sterile water and/or buffered solution(s) to remove residual amounts of acid and thereby raise the pH. A suitable defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to 40 percent by weight of water (i.e., about 60 to 90 weight percent of defatting agent such as alcohol) should be present in the defatting disinfecting solution to produce optimal lipid removal and disinfection within the shortest period of time. In a particular embodiment, the concentration range of the defatting solution is from about 60 to about 85 weight percent alcohol. In a further embodiment, the defatting solution is about 70 weight percent alcohol. In yet another embodiment, the cancellous bone is defatted in a solution of 1:1 chloroform:methanol at room temperature and then demineralized in 0.6 N HCl at 4° C.

The at least partially demineralized bone may be ground or otherwise processed into particles of an appropriate size before or after demineralization. In certain embodiments, the particle size is greater than 75 microns, ranges from about 100 to about 3000 microns, or ranges from about 100 to about 800 microns. After grinding the bone to the desired size, the mixture may be sieved to select those particles of a desired size. In certain embodiments, the bone particles may be sieved though a 50 micron sieve, a 75 micron sieve, or a 100 micron sieve.

Generally, demineralization conditions may affect the osteoinductivity of DBM. Proteases that degrade the osteoinductive activity of cortical bone have been described. Proteases present in cancellous bone have been shown to differ from those responsible for cortical bone remodeling. Thus, demineralization conditions utilized for cortical bone processing may not be ideal for cancellous bone. Specific protease inhibitor cocktails and lower temperatures may be used.

Following particulation, the bone may be treated to remove mineral from the bone as discussed above. While hydrochloric acid is commonly used as a demineralization agent, there are other methods for preparing DBM, which vary widely and include choices regarding the concentration of the demineralization agent; the temperature and duration of the demineralization step; the inclusion or exclusion at various points in the demineralization process of solvents or solvent combinations such as ethanol, methanol, and chloroform:ether; the extent to which the matrix is washed following the demineralization step; and whether the resulting DBM is stored frozen or is lyophilized and stored at room temperature. See, for example, Russell et al., 22(5) Orthopaedics 524-531 (1999), incorporated herein by reference.

Any of a variety of at least partially demineralized bone preparations may be used with the present invention. DBM prepared by any method may be employed, including particulate or fiber-based preparations, mixtures of fiber and particulate preparations, fully or partially demineralized preparations, mixtures of fully and partially demineralized preparations, and surface demineralized preparations. See U.S. Pat. No. 6,326,018; Reddi et al., 69 Proc. Natl. Acad. Sci. USA 1601-1605 (1972); Lewandrowski et al., 317 Clin. Ortho. Rel. Res. 254-262 (1995); Lewandroski et al., 31 J. Biomed. Mater. Res. 365-372 (1996); Lewandrowski et al. 61 Calcified Tiss. Int., 294-297 (1997); Lewandrowski et al., 15 I Ortho. Res. 748-756 (1997), each of which are incorporated herein by reference in their entireties. Suitable demineralized bone matrix compositions are described in U.S. Pat. No. 5,507,813, hereby incorporated by reference in its entirety. In some instances, large fragments or even whole bone may be demineralized, and then particulated following demineralization.

In some embodiments, the bone may be surface demineralized. The surface may be an inner surface, such as inside trabeculae or inside a Halversion canal. In other embodiments the surface may be an outer surface. In some embodiments, surface demineralized refers to the bone comprising at least one outer surface, or zone of an outer surface, that is demineralized and possessing a non-demineralized core. In some embodiments, the entirety of the surface may be partially demineralized. In other embodiments, a portion of the surface may be demineralized, such as by exposing only a portion of a particle to the demineralization process, by exposing a portion of the surface to a greater or lesser extent of the demineralization process, by masking, etc. Demineralization may be done to a certain percentage. In some embodiments, that percentage relates to weight percentage. In other embodiments, that percentage relates to percentage of the size of the bone being demineralized, or to the depth of demineralization. The depth of demineralization of the at least one outer surface thus may be viewed as a percentage of the size of the bone being demineralized or may be viewed as an absolute number.

Figure 2A:
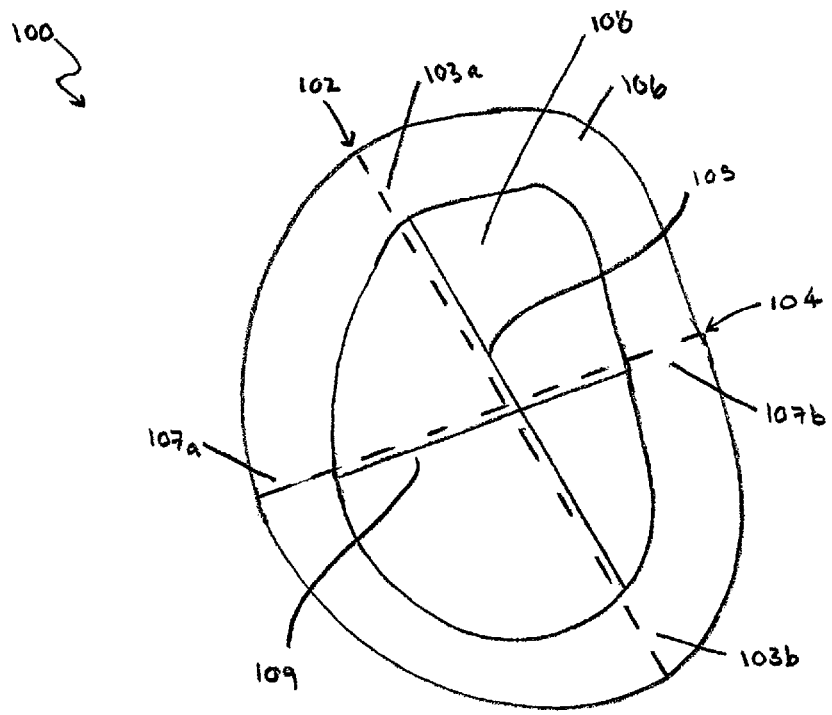
FIG. 2a illustrates a generally round bone particle wherein the bone particle has been surface demineralized in accordance with one embodiment.

Demineralization thus may be carried out to a percentage depth of the size of the bone being demineralized. FIGS. 4a and 4b illustrate surface demineralized bone particles. The bone particle 100 of FIG. 2a is substantially spherical. The bone particle 110 of FIG. 4b is somewhat elongate.

As shown, the bone particle 100 of FIG. 2a has a demineralized surface region 106 and a non-demineralized core 108. The bone particle 100 includes a length 102 along its longest dimension and a length 104 along its shortest dimension. The length 102 in the longest dimension comprises first and second demineralized portions 103a and 103b and a nondemineralized portion 105. A percentage of demineralization in the longest dimension may be determined by summing the length of the first and second demineralized portions 103a and 103b and dividing that total by the length 102 (comprising 103a, 103b and 105). The length 104 in the shortest dimension likewise comprises first and second demineralized portions 107a and 107b and a nondemineralized portion 109. A percentage of demineralization in the shortest dimension may be determined by summing the length of the first and second demineralized portions 107a and 107b and dividing that total by the length 104 (comprising 107a, 107b and 109). A total percentage demineralization may be determined by averaging the percent demineralization in the longest dimension with the percent demineralization in the shortest dimension.

Figure 2B:
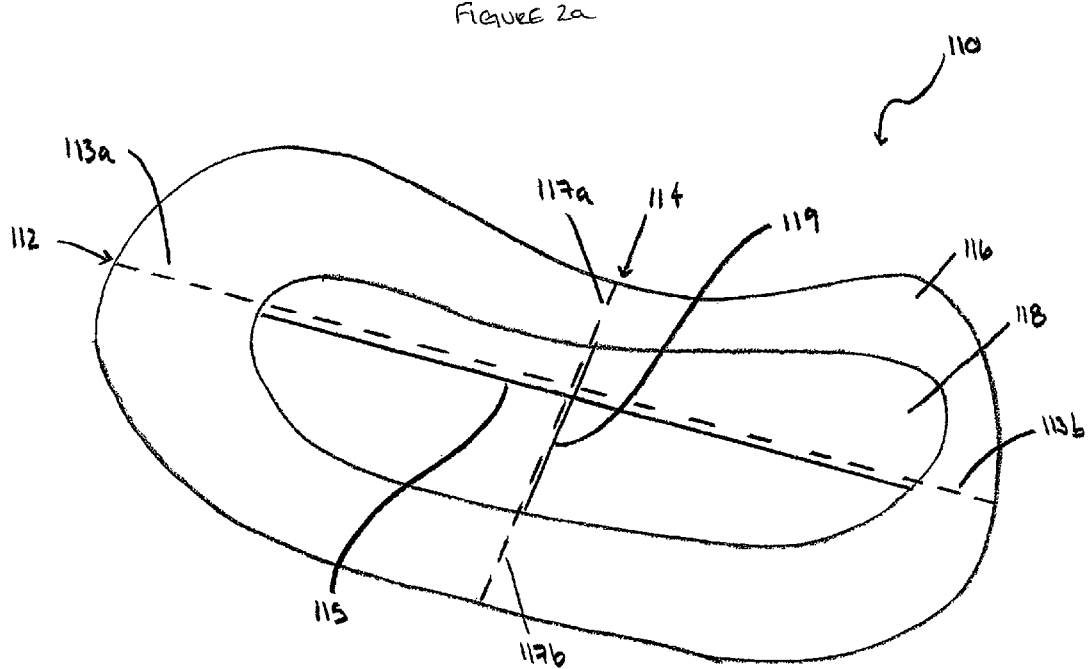
FIG. 2b illustrates an elongate bone particle wherein the bone particle has been surface demineralized in accordance with one embodiment.

As shown, the bone particle 110 of FIG. 2b has a demineralized surface region 116 and a non-demineralized core 118. The bone particle 110 includes a length 112 along its longest dimension and a length 114 along its shortest dimension. The longest dimension and shortest dimension are taken as those measuring largest and smallest, respectively, such as by a micrometer or using other by suitable manner and generally going through the center of the bone particle 110. The length 112 in the longest dimension comprises first and second demineralized portions 113a and 113b and a nondemineralized portion 115. A percentage of demineralization in the longest dimension may be determined by summing the length of the first and second demineralized portions 113a and 113b and dividing that total by the length 112 (comprising 113a, 113b, and 115). The length 114 in the shortest dimension likewise comprises first and second demineralized portions 117a and 117b and a nondemineralized portion 119. A percentage of demineralization in the shortest dimension may be determined by summing the length of the first and second demineralized portions 117a and 117b and dividing that total by the length 114 (comprising 117a, 117b, and 119). A total percentage demineralization may be determined by averaging the percent demineralization in the longest dimension with the percent demineralization in the shortest dimension.

Alternatively, percentage demineralization may be based on weight percent demineralized of total weight of the bone particle.

In some embodiments, demineralization may be carried out to a depth of, for example, at least about 100 microns. Surface demineralization may alternatively be done to a depth less than or more than about 100 microns. Generally, surface demineralization may be done to a depth of at least 50 microns, at least 100 microns, at least 200 microns, or other. Accordingly, in some embodiments, the demineralized bone comprises at least one outer surface possessing at least one demineralized zone and a non-demineralized core, wherein the demineralized zone of the outer surface of the bone may be, for example, at least about 100 microns thick. The demineralized zone may alternatively be less than or more than about 100 microns thick. The demineralized zone of the surface of the bone is osteoinductive, and therefore promotes rapid new ingrowth of native host bone tissue into an osteoimplant comprising surface demineralized bone. The osteoimplant may comprise surface demineralized monolithic bone or an aggregate of surface demineralized bone particles, and may be substantially solid, flowable, or moldable. The demineralized zone of the surface of the bone can be any surface portion.

When it is desirable to provide an osteoimplant having improved biological properties while still substantially maintaining the strength present in the osteoimplant prior to demineralization, for example where monolithic bone is used, the extent and regions of demineralization of the monolithic bone may be controlled. For example, depth of demineralization may range from at least about 100 microns to up to about 7000 microns or more, depending on the intended application and graft site. In some embodiments, the depth of demineralization is between 100 to about 5000 microns, between about 150 to about 2000 microns, or between about 200 microns to about 1000 microns. In alternative embodiments, depth of demineralization may be less than about 100 microns. Reference is made to U.S. Pat. No. 7,179,299, herein incorporated by reference for discussion of surface demineralization.

A benefit of surface demineralized bone is that the demineralized zone(s) can elastically yield under applied force while the mineralized core has strength and load bearing capacity exceeding that of demineralized bone. Thus, when the surface demineralized bone is subjected to an applied load, the demineralized zones can conform to contours of adjacent bone tissue and thereby minimize voids or spaces between the osteoimplant and adjacent bone tissue. This can be useful because host bone tissue will not grow to bridge large voids or spaces. Thus, by conforming to the contours of adjacent bone tissue, an osteoimplant comprising surface demineralized monolithic bone exhibits enhanced biological properties such as, for example, incorporation and remodeling. The non-demineralized inner core imparts mechanical strength and allows the monolithic osteoimplant to bear loads in vivo. Other non-demineralized zones provide improved tolerances when engaged with other objects such as, for example, insertion instruments, other implants or implant devices, etc. It is noted that some of these characteristics may also be exhibited by an osteoimplant comprising an aggregate of surface-demineralized bone particles.

IV. Enhancing Osteoinductive Properties

In certain embodiments, the treatment or condition alters a biological activity of the at least partially demineralized bone such that the at least partially demineralized bone displays osteoinductive, osteogenic, and/or chondrogenic activity in a species in which a control matrix (e.g., an inactivated matrix or a matrix not exposed to the treatment or condition) does not show such activity, or shows it in a lesser amount. For example, at least partially demineralized bone exposed to the treatment or condition may display increased osteoinductive, osteogenic, and/or chondrogenic activity in human, dog, squirrel monkey, etc., as assessed either in vitro or in vivo. Specifically, in some embodiments, cancellous bone, which is understood to have little to no osteoinductivity, as treated herein displays osteoinductive capacity.

Altering the Structure of the at Least Partially Demineralized Bone

In one embodiment, the structure of the at least partially demineralized bone may be altered to make growth factors within the bone more accessible. Thus, the at least partially demineralized bone may be contacted with a cleavage agent, e.g., a protease such as collagenase(s) or a chemical agent such as cyanogen bromide. The cleavage agents may be applied either together or sequentially, optionally washing the matrix between application of different agents to remove residual agent. In general, the biological and chemical agents may be used in an effective amount and for a time sufficient to achieve a desired outcome, e.g., a desired increase in a biological activity of the matrix.

In one embodiment, treatment may be by limited digestion with purified bacterial collagenase. Collagenases and their activity on collagens of various types have been extensively studied. A number of collagenase preparations are available from Worthington Biochemical Corporation, of Lakewood, N.J. As is known in the art, collagen consists of fibrils composed of laterally aggregated, polarized tropocollagen molecules (MW 300,000). Each tropocollagen unit consists of three helically wound polypeptide α-chains around a single axis. The strands have repetitive glycine residues at every third position and numerous proline and hydroxyproline residues, with the particular amino acid sequence being characteristic of the tissue of origin. Tropocollagen units combine uniformly to create an axially repeating periodicity. Cross linkages continue to develop and collagen becomes progressively more insoluble and resistant to lysis on aging. Gelatin results when soluble tropocollagen is denatured, for example on mild heating, and the polypeptide chains become randomly dispersed. In this state the strands readily may be cleaved by a wide variety of proteases.

In the past, digestion of bone with purified bacterial collagenase has been used for altering the solubility of human DBM in cell culture media. Digestion of bone with purified bacterial collagenase has also been used to enhance the response of myoblastic cells to cortical human DBM.

As taught herein, cancellous DBM treated with collagenase has enhanced in vivo osteoinductive capacity. Collagenase treatment of cancellous human DBM increases its solubility relative to that of untreated cancellous human DBM. The solubility of the cancellous DBM may be increased by exposure to an appropriate treatment or condition, e.g., collagenase treatment, radiation, heat, or any other suitable treatment and/or condition, etc. The extent to which the solubility is increased may be varied by varying the nature of the treatment (e.g., the enzyme concentration) and/or the time over which it is applied. In some implementations, the cancellous DBM may be partially solubilized by the collagenase, while in others, the cancellous DBM may be completely solubilized by the collagenase.

According to various embodiments, a combination of treatments may be used. For example, the partially digested at least partially demineralized bone may be treated with heat or pepsin or another protease to disrupt cross-links not disrupted by the collagenase. The at least partially demineralized bone may be exposed to a variety of biological agents in addition to, or instead of, one or more proteases. Other enzymes include methylases, acylases, lipases, phospholipases, endo- and exo-glycosidases, glycanases, glycolases, amylase, pectinases, galacatosidases, etc. Chemical agents that perform similar reactions may be used. For example, a number of different alkylating agents are known. A variety of salts present in high concentrations (e.g., at least 6 M, 7M, 8M, etc.) may be used. Exemplary salts include salts of various Group I elements, e.g., LiCl. Denaturing agents, e.g., denaturing salts such as guanidinium HCl, may be used. Where denaturing agents are used, care should be taken to avoid denaturing desired components present in the matrix, e.g., growth factors.

A variety of different collagenases known in the art may be used. Collagenases are classified in section 3.4.24 under the International Union of Biochemistry and Molecular Biology (NC-IUBMB) enzyme nomenclature recommendations (see, e.g., 3.4.24.3, 3.4.24.7, 3.4.24.19). The collagenase may be of eukaryotic (mammalian) or prokaryotic (bacterial) origin. Bacterial enzymes differ from mammalian collagenases in that they attack many sites along the helix. Collagenase may cleave simultaneously across all three chains or attack a single strand. Generally, the collagenase cleaves Type I collagen, e.g., degrades the helical regions in native collagen, at the Y-Gly bond in the sequence Pro-Y-Gly-Pro-, where Y is most frequently a neutral amino acid. This cleavage yields products susceptible to further peptidase digestion. Any protease having one or more of these activities associated with collagenase may be used as a collagenase in accordance with the present invention.

It will be appreciated that crude collagenase preparations contain not only several collagenases, but also a sulfhydryl protease, clostripain, a trypsin-like enzyme, and an aminopeptidase. This combination of collagenolytic and proteolytic activities is effective at breaking down intercellular matrices, the essential part of tissue disassociation. Crude collagenase is inhibited by metal chelating agents such as cysteine, EDTA, or o-phenanthroline, but not DFP. It is also inhibited by α2-macroglobulin, a large plasma glycoprotein. $Ca^{2+}$ is required for enzyme activity. Therefore, it may be desirable to avoid collagenase inhibiting agents when treating at least partially demineralized bone with collagenase. In addition, although the additional proteases present in some collagenase preparations may aid in breaking down tissue, they also may cause degradation of desired matrix constituents such as growth factors. Therefore, it may be desirable to use a highly purified collagenase that contains minimal secondary proteolytic activities along with high collagenase activity. For example, a collagenase preparation may contain at least 90%, at least 95%, at least 98%, or at least 99% collagenase by weight. The preparation may be essentially free of bacterial components, particularly bacterial components that could cause inflammatory or immunological reactions in a host, such as endotoxin, lipopolysaccharide, etc. Preparations having a purity greater than 99.5% may be used. It may be desirable to include various protease inhibitors that do not inhibit collagenase but that inhibit various proteases that digest BMP. For example, protease inhibitors that are known to protect BMP activity from degradation include N-ethyl maleimide, benzamidine hydrochloride, iodoacetic acid, PMSF, AEBSF, and E-64. Bestatin may also be used, particularly if the preparation contains aminopeptidase activity. Any of these protease inhibitors (or others) may be included in a carrier, such as a bone matrix composition, or in any composition that is used to treat a carrier.

As discussed above, collagenase disrupts crosslinks between collagen. Using highly purified collagenase, it is possible that not all the crosslinks are disrupted. Generally, different grades of collagenase may disrupt different ranges of crosslinks. Thus, other treatments, such as pepsin treatment or heat treatment, may be used to disrupt crosslinks not affected by the collagenase.

In alternative embodiments, any suitable compound for altering the structure of the DBM may be used. For example, enzymes (e.g., pepsin) or chemicals may be used. Pepsin alters the structure of Type I collagen by cleaving the associated telopeptides. Further, mechanical means such as ionizing radiation or electromagnetic radiation may be used.

Another suitable protease is bone morphogenetic protein 1 (BMP-1). BMP-1 is a collagenolytic protein that has also been shown to cleave chordin (an inhibitor of BMP-2 and BMP-4). Thus, BMP-1 may be of use to alter the physical structure of the DBM (e.g., by breaking down collagen) and/or to cleave specific inhibitory protein(s), e.g., chordin or noggin. Proteins related to any of the proteases described herein, i.e., proteins or protein fragments having the same cleavage specificity, also may be used. It will be appreciated that variants having substantial sequence identity to naturally occurring protease may be used. For example, variants at least 80% identical over at least 50%, at least 60%, at least 70%, at least 80%, at least 90%, or 100% of the length of naturally occurring protease (or any known active fragment thereof that retains cleavage specificity) when aligned for maximum identity allowing gaps may be used.

Certain proteases that may provide desirable effects include members of the proprotein convertase (PPC) family of proteases, such as furin and related proteases. Members of this family of cellular enzymes cleave most prohormones and neuropeptide precursors. Numerous other cellular proteins, some viral proteins, and bacterial toxins that are transported by the constitutive secretory pathway are also targeted for maturation by PCs. Furin and other PC family members share structural similarities that include a heterogeneous ~10 kDa amino-terminal proregion, a highly conserved ~55 kDa subtilisin-like catalytic domain, and carboxyl-terminal domain that is heterogeneous in length and sequence. These enzymes become catalytically active following proregion cleavage within the appropriate cellular compartment. Furin is the major processing enzyme of the secretory pathway and is localized in the trans-golgi network. van den Ouweland, A. M. W. et al., 18 Nucl. Acid Res. 664 (1990); Steiner, D. F., 2 Curr. Opin. Chem. Biol. 31-39 (1998). Substrates of furin include blood clotting factors, serum proteins, and growth factor receptors such as the insulin-like growth factor receptor. Bravo D. A. et al., 269 J. Biol. Chem. 25830-25873 (1994). The minimal cleavage site for furin is Arg-X-X-Arg. However, the enzyme prefers the site Arg-X-(Lys/Arg)-Arg. An additional arginine at the P6 position appears to enhance cleavage. Krysan D. J. et al., 274 J. Biol. Chem. 23229-23234 (1999). Furin is inhibited by EGTA, α1-antitrypsin Portland, Jean, F. et al., 95 Proc. Natl. Acad. Sci. USA 7293-7298 (1998), and polyarginine compounds, Cameron, A. et al., 275 J. Biol. Chem. 36741-36749 (2000). Furin has been shown to proteolytically process both proTGF and proBMP proteins, for example, proTGF-β and proBMP-4, respectively, resulting in the release of the active mature form for each molecule. Dubois et al., 158(1) Am. J. of Pathology 305-316 (2001); Cui et al., 17(16) Embo Journal 4735-4743 (1998); Cui et al., 15 Genes & Development 2797-2802 (2001), each incorporated by reference herein in their entireties. Furin has also been shown to cleave BMP-2, BMP-6, and BMP-7. For example, furin cleaves between amino acids 282 and 283 in mature human BMP-2. Newly synthesized human BMP-2 contains a signal sequence (amino acids 1-23), a propeptide (amino acids 24-282), and an active portion (amino acids 283-396). Furin cleaves mature BMP-2 (amino acids 24-396) between amino acids 282 and 283 to release the propeptide and the active molecule.

Thus, the at least partially demineralized bone may be treated with PPCs such as furin and/or other proteases, which process immature TGF-β and/or BMP superfamily propeptides into their active mature forms and/or process active or inactive TGF-β and/or BMP superfamily polypeptides into smaller active fragments that are resistant to degradation or inactivation relative to the longer polypeptide, generating at least partially demineralized bone with increased osteoinductivity compared to at least partially demineralized bone lacking the protease, resulting in improved bone formation. The higher titers of the mature and/or degradation resistant species in these preparations increase the osteoinductive capacity of the at least partially demineralized bone.

At least partially demineralized bone may be exposed to any of the enzymes, e.g., proteases described herein (and others) at a range of different concentrations, e.g., between 1 pg/ml-100 μg/ml. For example, a protease may be used at between 1 pg/ml-100 pg/ml, between 100 pg/ml and 1 ng/ml, between 1 ng/ml and 100 ng/ml, between 100 ng/ml and 1 μg/ml, between 1 μg/ml and 100 μg/ml, etc. A variety of different digestion buffers may be used. The time of digestion may vary according to the protease, amount of DBM, and desired degree of digestion. In general, suitable times range between 30 minutes to 72 hours, e.g., between 30 minutes to 1 hour, between 1 and 12 hours, between 12 and 24 hours, between 24 and 48 hours, between 48 and 72 hours, etc. It will be appreciated that these times are approximate. Determination of the optimal treatment times for any preparation may involve assay of the treated tissue preparation in one of the biological activity assays described herein or others known in the art.

Allogenic cancellous demineralized bone is known not to be osteoinductive. Schwarz et al., 111(1) Arch Orthop Trauma Surg. 47-50 (1991). Applicants have made the surprising discovery that allogenic cancellous bone, when treated with collagenase enzymes for approximately one hour, becomes osteoinductive, approximately as osteoinductive as allogenic cortical demineralized bone. Thus, the bone, whether cancellous, corticocancellous, or cortical, may be treated for any suitable time period to enhance its osteoinductivity, including from about 15 minute to about 3 hours, from about 30 minutes to about 90 minutes, or for about 60 minutes. While not desiring to be bound by any particular scientific theory, applicants state that it is believed that the disruption of the collagen matrix makes osteoinductive factors bioavailable. Many types of collagenalytic enzymes, such as those set forth herein, would be expected to render allogenic at least partially demineralized bone osteoinductive when treated as described herein. Other treatments alternatively may be used and also are expected to provide the same result, including the use of salts or ionizing or electromagnetic radiation, or various categories of enzymes, so long as the enzymes disrupt the collagen without damaging the osteoinductive factors.

In addition, the osteoinductive capacity of DBM preparations in higher order species, such as squirrel monkeys, dogs, and humans, has been questioned. For example, allogeneic cancellous bone blocks, demineralized or not, have no osteoinductive capacity and no osteoconductive function that promotes healing of mid-diaphyseal bone defects in dogs. Schwarz et al., 111(1) Arch. Orthop. Trauma Surg. 47-50 (1991). Adult monkey bone matrix contains bone inductive properties, but these properties are not sufficient to induce bone formation in adult monkey muscle sites. Aspenberg et al., 63(6) Acta Orthop Scand. 619-622 (1992); see also Aspenberg et al., 9(1) J. Orthop. Res. 20-5 (1991); Schmid et al., 19(1) Unfallchirurgie 1-8 (1993); Toriumi et al., 116(6) Arch Otolaryngol Head Neck Surg. 676-680 (1990); and Ousterhout, D K, 15(5) Ann. Plast Surg. 367-373 (1985). Structural modifications of demineralized bone collagen may serve to activate the latent osteoinductive potential of DBM preparations in higher order species. Such products, irrespective of whether derived from cancellous or cortical bone, may have significantly enhanced clinical efficacy in a variety of orthopaedic applications as observed by more rapid bone healing and spinal fusion.

The at least partially demineralized bone may be exposed to a physical condition instead of, or in addition to, a biological or chemical agent. For example, the at least partially demineralized bone may be exposed to heat or cold for a suitable period of time, e.g., minutes, hours, or up to several days, where "heat" refers to temperatures above room temperature (about 23-25 degrees C.) and "cold" refers to temperatures below room temperature. Cycles of temperature change may be used, e.g., the at least partially demineralized bone may be heated and cooled a plurality of times. The temperature may, for example, be at least 37 degrees C., at least 40, 50, 60, 70, 80, or 90 degrees C. In some embodiments, the heat treatment may be relatively gentle to avoid denaturing growth factors and other factors, typically proteins or peptides, that contribute to the osteogenic, osteoinductive, or chondrogenic activity of the matrix. The temperature may be 20 degrees C. or below, 15 degrees C. or below, 10 degrees C. or below, 0 degrees C. or below, etc. In general, the at least partially demineralized bone may be exposed to any desired temperature in the presence or absence of other agents, solvents, or other suitable media. The at least partially demineralized bone may be exposed to electromagnetic energy of any type, e.g., X-rays and microwaves. Gamma-rays, beta-rays, or any suitable ionizing radiation may be used. The treatment may be performed in the absence of oxygen or in a reduced oxygen environment. U.S. patent application Ser. No. 12/140,062 to Method of Treating Tissue, filed Jun. 16, 2008, is herein incorporated by reference in its entirety for the purposes of all that is disclosed therein.

In certain embodiments, the treatment or condition alters the physical structure of the matrix so as to increase its biological activity. The treatment or condition may alter the structure of the at least partially demineralized bone so as to facilitate the presentation of such molecules, e.g., on a surface of the at least partially demineralized bone. The treatment or condition may alter the conformation of such molecules in a manner that facilitates interactions with target cells, e.g., cells that migrate towards or into the bone matrix. The treatment or condition may alter release kinetics of agents such as growth factors, differentiation factors, chemotactic factors, etc., from the matrix. Exemplary factors that up-regulate collagen synthesis by osteoblasts include TGF-β, PDGF, IGF, IL-1, $PGE_2$, and certain BMPs. Certain treatments may alter, e.g., increase, the affinity of bone and/or cartilage forming cells and/or undifferentiated cells capable of differentiation into bone and/or cartilage forming cells for the matrix. For example, the treatment or condition may alter integrin binding sites (such as RGD sequences), e.g., by making them more available to cells.

In certain embodiments, alteration of the structure involves cleavage or partial degradation of one or more major structural component of the matrix such as collagen, e.g., components that typically make up at least 1%, 5%, 10%, 25%, 50%, 75%, 90% etc., of the dry weight of the at least partially demineralized bone. In certain embodiments, the secondary, tertiary, and/or quaternary structure of a major structural component of the matrix is altered. The alteration may include destruction of bonds that normally maintain the triple helical structure of collagen, bonds that hold collagen fibrils together, etc. DBM is a dense structure held together by cross-linked collagen. Most of the noncollagenous proteins (NCPs) are trapped within and/or attached to this framework. Certain agents such as collagenase may cut across the framework and thereby potentially allow access to the NCPs. The amount of collagen (or other structural protein) that is cleaved and/or degraded may vary. For example, in certain embodiments, at least 10%, at least 25%, at least 50%, at least 75%, or at least 90% of the collagen originally present in the DBM is cleaved or degraded. Between 10-25%, 25-50%, 50-75%, 75-90%, 90-100%, or any other suitable range such as 10-90%, 25-75%, etc., of the collagen may be cleaved or degraded. A polypeptide is considered to be cleaved if it is cleaved at a single site or at multiple sites. In certain embodiments, the cleavage cleaves a crosslink. In certain embodiments, at least a portion of the collagen is present as collagen fragments. For example, at least 10%, at least 25%, at least 50%, at least 75%, at least 90%, etc., of the collagen is present as collagen fragments in certain embodiments. Between 10-25%, 25-50%, 50-75%, 75-90%, 90-100%, or any other range such as 10-90%, 25-75%, etc., of the collagen may be present as collagen fragments. The fragments may remain associated with or present in or on the bone matrix or may diffuse away. A bone matrix may be exposed to any of a variety of different biological or chemical agents or conditions for different time periods in order to achieve a desired degree of cleavage or degradation of a structural component of the matrix such as collagen. The invention therefore provides a modified bone matrix comprising a collagen-containing bone matrix, wherein at least a portion of the collagen is cleaved or degraded. Matrices in which at least a portion of a different structural component of the matrix is cleaved or degraded are also provided.

In certain embodiments, the at least partially demineralized bone may be exposed to a treatment or condition that generates peptides and protein fragments having osteoinductive or chondrogenic activity. In contrast to various longer proteins, certain peptides and protein fragments are less susceptible to proteolytic degradation and more likely to maintain their osteoinductive or chondrogenic properties in the proteolytic environment of the matrix or implant site. Many osteoinductive and chondrogenic proteins, for example, growth factors such as BMPs, cell signaling molecules, transcription factors, hormones, etc., have domains that are responsible for binding to receptors and/or initiating signal transduction in bone and cartilage growth pathways. These domains are capable of functioning independently as peptides and protein fragments. In certain embodiments, the present invention increases the osteoinductive or chondrogenic activity of bone and cartilage matrices by cleaving the osteoinductive and chondrogenic factors present in the matrix to generate active peptides or protein fragments and/or to generate active peptides or protein fragments that are less susceptible to degradation than their longer precursors. The increased number of factors in the matrix results in increased bone or cartilage formation.

Compacting the Structure

The at least partially demineralized bone may be compacted to increase the growth factor concentration gradient of the at least partially demineralized bone. Thus, by compressing the structure of bone, the osteoinductive potential may be increased. Compression may be achieved via any suitable mechanism. For example, compression may be achieved by mechanical means, heat, chemical modification of the collagenous structure or any suitable type of compression processing. In one embodiment, the bone is compacted by grinding or otherwise processing the bone into particles of an appropriate size and formed into a dense bone structure. In another embodiment, the bone is compacted by treatment with LiCl, thereby shrinking the structure.

Cancellous DBM has a sponge-like structure. Accordingly, in some embodiments, use of compression may be particularly suitable for cancellous bone. While the DBM may be compressed, typically when contacted with a liquid the DBM returns to its pre-compressed state. To prevent the DBM from returning to its pre-compressed state, the DBM may be provided in a container for maintaining force on it. Thus, for example, it may be placed in a defect, mesh, chamber, cage, etc. In accordance with some embodiments, the pressed DBM structure may be specifically configured to retain its shape in water for a predetermined amount of time. For example, the pressed DBM structure may be configured to retain its shape in water for one or more hours, up to seven hours, up to several days, e.g., 48, 72 or 96 hours, or up to one week or several weeks.

The osteoinductive at least partially demineralized bone may be used in an expandable osteoimplant such as taught by PCT Application No. PCT/US2006/001540, filed Jan. 17, 2006, hereby incorporated by reference in its entirety. As disclosed in that application, an osteoimplant comprising demineralized bone particles has a first state and an expanded state. The osteoimplant may be used with another device or on its own. In the first state, the osteoimplant may be inserted into a device such as an intervertebral body fusion device. The osteoimplant may be rehydrated to expand to an increased size, for example as far as permitted by the confines of the intervertebral body fusion device and spinal endplates, thereby aiding in greater vertebral endplate contact and conformity in spinal surgery. In addition or alternatively, rehydration may take place in vivo. The osteoimplant may comprise fully or partially demineralized cancellous bone and fully and/or partially demineralized cortical bone. In one embodiment, the cancellous bone is provided in chips, and the cortical bone in fibers. The demineralized cancellous bone may comprise, in whole or part, osteoinductive cancellous DBM as taught herein. In another embodiment, the expandable osteoimplant may comprise, in whole or in part, cancellous DBM, some or all of which may be made osteoinductive pursuant to the present invention. In yet a further embodiment, the expandable osteoimplant may comprise a monolithic piece of bone treated as provided herein, such as by at least partially demineralizing and treating the monolithic piece of bone.

In one embodiment, the compressed at least partially demineralized bone is provided by grinding the bone, for example into a fine powder, and molding it into a cohesive shape. The bone may be wetted and processed to a consistency of a fibrous paste before molding. In one embodiment, the molding is done via hand molding and drying the material at ambient temperature. In another embodiment, the molding is done by putting the bone in a mold, such as a polyurethane or PTFE mold, putting the mold under pressure, for example by clamping the mold, and allowing the bone to dry, for example via vacuum drying the material at 40° C. for 72 hours. In yet another embodiment, the molding is done by putting the bone into a stainless steel mold, pressing the mold with 500 pounds and vacuum drying the mold at 40° C. for 72 hours with weighted dehydrothermal plungers.

Thus, in various embodiments, the DBM may be ground to a powder-like consistency, processed into a fibrous paste, and the fibrous paste compressed and dried. Compression and drying may be done in any suitable manner. For example, compression may be done by applying manual pressure, by clamping (powered manually, through dehydrothermal plungers, or other), or other means. Drying may be done in air at ambient temperature, in an oven, vacuum dried, or in any other suitable manner.

In another embodiment, the at least partially demineralized bone is compacted by treatment with LiCl to shrink the collagenous structure. Specifically, at least partially demineralized bone may be treated with 8M LiCl to increase the osteoinductivity of the at least partially demineralized bone. Treatment with LiCl may further increase the radioopacity of the at least partially demineralized bone.

V. Osteoimplant

Bone grafting applications are differentiated by the requirements of the skeletal site. Certain applications generally use a "structural graft" in which one role of the graft is to provide mechanical or structural support to the site. Such grafts contain a substantial portion of mineralized bone tissue to provide the strength needed for load-bearing. Examples of applications requiring a "structural graft" include intercalary grafts, spinal fusion, joint plateaus, joint fusions, large bone reconstructions, etc. Other applications generally use an "osteogenic graft," in which one role of the graft is to enhance or accelerate the growth of new bone tissue at the site. Such grafts contain a substantial portion of demineralized bone tissue to improve the osteoinductivity needed for growth of new bone tissue. Examples of applications requiring "osteogenic graft" include deficit filling, spinal fusions, joint fusions, etc. Grafts may also have other beneficial biological properties, such as, for example, serving as delivery vehicles for bioactive substances. Bioactive substances include physiologically or pharmacologically active substances that act locally or systemically in the host.

In accordance with various embodiments, the at least partially demineralized bone matrix provided herein may be used as a structural graft, an osteogenic graft, or a graft suitable for both structural and osteogenic uses.

Any suitable shape, size, and porosity of at least partially demineralized bone may be used. In various embodiments, the bone may be monolithic or may be composite. Rat studies show that the new bone is formed essentially having the dimensions of the device implanted. A successful osteoimplant for encouraging bone development appropriately accommodates each step of the cellular response during bone development, and in some cases, protects osteoinductive factors from nonspecific proteolysis. In some uses, the osteoimplant acts as a temporary scaffold until replaced completely by new bone. In bone, the dissolution rates may vary according to whether the implant is placed in cortical or trabecular bone.

The osteoimplant resulting from the at least partially demineralized bone may assume a determined or regular form or configuration such as a sheet, plate, disk, tunnel, cone, tube, a rod, string, weave, solid, fiber, or wedge, to name but a few. Prefabricated geometries include, but are not limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, wave plates. Partial tubular as well as flat plates may be fabricated from the osteoimplant. Such plates may include such conformations as, e.g., concave contoured, bowl shaped, or defect shaped.

In certain embodiments, the shape and size of the particles in the carrier affect the time course of osteoinductivity. For example, in a cone or wedge shape, the tapered end will result in osteoinductivity shortly after implantation of the osteoimplant, whereas the thicker end will lead to osteoinductivity later in the healing process (hours to days to weeks later). Also, larger particle size will have induce bone formation over a longer time course than smaller particles. Particles of different characteristics (e.g., composition, size, shape) may be used in the formation of these different shapes and configurations. For example, in a sheet of DBM a layer of long half-life particles may be alternated between layers of shorter half-life particles. See U.S. Pat. No. 5,899,939, herein incorporated by reference in its entirety, for suitable examples. In a weave, strands composed of short half-life particles may be woven together with strands of longer half-lives.

The osteoimplant may be machined or shaped by any suitable mechanical shaping means. Computerized modeling may provide for the intricately-shaped three-dimensional architecture of an osteoimplant custom-fitted to the bone repair site with precision.

Thus, the at least partially demineralized bone may optionally be subjected to a configuring step to form an implant. In an embodiment wherein the bone is compressed to enhance osteoinductivity, the configuring step may be done during compression. The configuring step may be employed using conventional equipment known to those skilled in the art to produce a wide variety of geometries, e.g., concave or convex surfaces, stepped surfaces, cylindrical dowels, wedges, blocks, screws, and the like. A surgically implantable material fabricated from elongated bone particles that have been demineralized, which may be shaped as a sheet, and processes for fabricating shaped materials from demineralized bone particles are disclosed in U.S. Pat. Nos. 5,507,813 and 6,436,138, respectively, the contents of which are incorporated by reference herein in their entireties. Suitable sheets include those sold under the trade name Grafton® DBM Flex, which must be wetted/hydrated prior to use to be useful for implantation. Such sheets have recently been reported as effective in seeding human bone marrow stromal cells (BMSCs), which may be useful in the repair of large bone defects. Kasten et al., *Comparison of Human Bone Marrow Stromal Cells Seeded on Calcium-Deficient Hydroxyapatite, Betatricalcium Phosphate and Demineralized Bone Matrix,* 24(15) Biomaterials 2593-2603 (2003). Also useful are demineralized bone and other matrix preparations comprising additives or carriers such as binders, fillers, plasticizers, wetting agents, surface active agents, biostatic agents, biocidal agents, and the like. Some exemplary additives and carriers include polyhydroxy compounds, polysaccharides, glycosaminoglycan proteins, nucleic acids, polymers, polaxomers, resins, clays, calcium salts, and/or derivatives thereof. See, for example, U.S. Pat. No. 5,290,558, incorporated by reference herein in its entirety.

The bone used in creating the at least partially demineralized bone may be obtained from any source of living or dead tissue. In many instances, the source of bone may be matched to the eventual recipient of the inventive composition. At a minimum, it is often desirable that the donor and recipient are of the same species, though even xenogenic sources are permitted. Thus, for use in humans, generally DBM derived at least in part from human bone may be used. For example, bone material may be at least 10%, 20%, 30%, 40%, 50%, 60%, 70%, 80%, 90% or more human bone material. In certain embodiments 100% of the bone material is human bone material.

In one embodiment, the osteoimplant induces endochondral bone formation reliably and reproducibly in a mammalian body. The at least partially demineralized bone osteoimplant comprises particles of porous materials. The pores must be of a dimension to permit progenitor cell migration into the carrier and subsequent differentiation and proliferation. The particle size may be within the range of 70 μm-850 μm, or 70 μm-420 μm, or 150 μm-420 μm, though any suitable size may be used. It may be fabricated by close packing particulate material into a shape spanning the bone defect, or by otherwise structuring as desired a material that is biocompatible, and in some embodiments biodegradable in vivo to serve as a "temporary scaffold" and substratum for recruitment of migratory progenitor cells, and as a base for their subsequent anchoring and proliferation.

VI. Formulation

The osteoinductive at least partially demineralized bone or the osteoimplant may be formulated for a particular use. The formulation may be used to alter the physical, biological, or chemical properties of the DBM. A physician would readily be able to determine the formulation needed for a particular application, taking into account such factors as the type of injury, the site of injury, the patient's health, and the risk of infection. In various embodiments, the at least partially demineralized bone may comprise, for example, less than approximately 0.5% water, less than approximately 1% water, or less than approximately 5% water.

The osteoinductive at least partially demineralized bone may be configured to be suturable. Thus, in certain embodiments, the osteoinductive at least partially demineralized bone or an osteoimplant formed from the osteoinductive at least partially demineralized bone may be sutured in place in vivo.

An osteoimplant formed from osteoinductive cancellous DBM may be configured for expansion. Cancellous DBM has a sponge-like texture and expands and conforms. Thus, an osteoimplant may be formed that is able to expand and conform to a site in vivo. The osteoimplant so formed may comprise monolithic cancellous bone or particulated (and reaggregated) cancellous bone.

Osteoinductive at least partially demineralized bone or osteoimplants may be prepared to have selected resorption/loss of osteoinductivity rates, or even to have different rates in different portions of an implant. For example, the formulation process may include the selection of bone particles of a particular size or composition, combined with the selection of a particular stabilizing agent or agents and the amounts of such agents.

Physical properties such as deformability and viscosity may also be chosen depending on the particular clinical application. The particles of bone may be mixed with other materials and factors to improve other characteristics of the implant. For example, the at least partially demineralized bone material may be mixed with other agents to improve wound healing. These agents may include drugs, proteins, peptides, polynucleotides, solvents, chemical compounds, and biological molecules.

In another embodiment, an osteoimplant having a preselected three-dimensional shape is prepared by repeated application of individual layers of DBM, for example by 3-D printing as described by U.S. Pat. Nos. 5,490,962, 5,518,680, and 5,807,437, each incorporated herein by reference in their entireties. Different layers may comprise individual stabilized DBM preparations, or alternatively may comprise DBM layers treated with stabilizing agents after deposition of multiple layers.

In the process of preparing improved inventive bone matrix materials, the materials may be produced entirely aseptically or be sterilized to eliminate any infectious agents such as HIV, hepatitis B, or hepatitis C. The sterilization may be accomplished using antibiotics, irradiation, chemical sterilization (e.g., ethylene oxide), super critical $CO_2$ treatment, thermal sterilization, or combinations thereof. Other methods known in the art of preparing bone and cartilage matrices, such as defatting, sonication, lyophilization, and combinations thereof may also be used. Since the biological activity of various materials including demineralized bone is known to be detrimentally affected by most terminal sterilization processes, care must be taken when sterilizing the inventive compositions. In some embodiments, the osteoimplants described herein will be prepared aseptically or sterilized.

VII. Optional Treatments

In other embodiments, the present invention provides methods of increasing the osteoinductivity of the at least partially demineralized bone by further exposing the at least partially demineralized bone to at least one treatment (e.g., a biological or chemical agent). In addition to treatment with collagenase (or other suitable compound) or compaction, the at least partially demineralized bone may be exposed to a chemical or condition that selectively degrades inhibitors of osteogenic activity and/or to a chemical or condition that activates osteoinductive factors in the carrier. Thus, the resulting at least partially demineralized bone has an increased osteoinductivity, osteogenic, or chondrogenic activity compared to a similar at least partially demineralized bone not exposed to the treatment or condition, because inhibition of an osteoinductive, osteogenic, or chondrogenic factor is blocked. In general, agents that inhibit or reduce osteoinductive, osteogenic, or chondrogenic activity may be referred to as bone/cartilage inhibitory factors (BCIF).

Generally, it may be desirable to remove the inhibitors quickly without denaturing the osteoinductive factors. As will be appreciated by those skilled in the art, factors having osteoinductive, osteogenic, and/or chondrogenic activity may be inhibited by a variety of mechanisms including proteolytic degradation, binding or sequestration of the factor, etc.

VIII. Optional Additives

Optionally, other additives may be included in the osteoinductive at least partially demineralized bone. It will be appreciated that the amount of additive used will vary depending upon the type of additive, the specific activity of the particular additive preparation employed, and the intended use of the at least partially demineralized bone. The desired amount is readily determinable by the user. Any of a variety of medically and/or surgically useful optional substances may be incorporated in, or associated with, the osteoinductive factors either before, during, or after preparation of the at least partially demineralized bone.

In certain embodiments, the additive is adsorbed to or otherwise associated with the osteoimplant. The additive may be associated with the osteoimplant through specific or non-specific interactions, or covalent or noncovalent interactions. Examples of specific interactions include those between a ligand and a receptor, an epitope and an antibody, etc. Examples of nonspecific interactions include hydrophobic interactions, electrostatic interactions, magnetic interactions, dipole interactions, van der Waals interactions, hydrogen bonding, etc. In certain embodiments, the additive is attached to the osteoimplant, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the DBM. In another embodiment, the additive is attached to an antibody, or fragment thereof, that recognizes an epitope found within the DBM. An additive may be provided within the osteoimplant in a sustained release format. For example, the additive may be encapsulated within biodegradable nanospheres, microspheres, or the like.

It will be understood by those skilled in the art that the lists of optional substances herewith included are not intended to be exhaustive and that other materials may be admixed with bone-derived elements within the practice of the present invention.

Osteoinductive Factors

Osteoinductive factors may be added to the treated at least partially demineralized bone, thus further increasing the osteoinductivity of the at least partially demineralized bone. U.S. patent application Ser. No. 11/555,608, entitled Bone Matrix Compositions and Methods, filed Nov. 1, 2006, which is herein incorporated by reference in its entirety, teaches suitable methods for adding osteoinductive factors to the at least partially demineralized bone and for otherwise enhancing the osteoinductivity of the bone.

Osteoinductive factors include any agent that leads to or enhances the formation of bone. The osteoinductive factors may do this in any manner. For example, the osteoinductive factors may lead to the recruitment of cells responsible for bone formation, the osteoinductive factors may lead to the secretion of matrix which may subsequently undergo mineralization, the osteoinductive factors may lead to the decreased resorption of bone, etc. Suitable osteoinductive factors include bone morphogenic proteins (BMPs), transforming growth factor (TGF-0), insulin-like growth factor (IGF-1), parathyroid hormone (PTH), and angiogenic factors such as VEGF. In one embodiment, the osteoinductive factors is genetically engineered to comprise an amino acid sequence which promotes the binding of the inducing agent to the DBM or the carrier. Sebald et al., PCT/EP00/00637, incorporated herein by reference in its entirety, describe the production of exemplary engineered growth factors suitable for use with DBM.

Other osteoinductive factors also may be added to the at least partially demineralized bone. These osteoinductive factors may be added in an activated or nonactivated form, and they may be added at anytime during the preparation of the inventive material. For example, the osteoinductive factors may be added after the demineralization step and prior to the addition of the stabilizing agents so that the added osteoinductive factors are protected from exogenous degrading enzymes once implanted. In some embodiments, the at least partially demineralized bone is lyophilized in a solution containing the osteoinductive factors. In certain other embodiments, the osteoinductive factors are adhered onto the hydrated demineralized bone matrix and are not freely soluble. In other instances, the osteoinductive factors are added after addition of a stabilizing agent so that the osteoinductive factors are available immediately upon implantation of the at least partially demineralized bone.

Radiopaque Substances

Radiopaque substances may be added to impart radiopacity to the at least partially demineralized bone. Examples of substances imparting radiopacity include for example, fully mineralized bone particles, Barium- and Iodine-containing compounds or compositions, e.g., barium sulfate and barium sulfate for suspension, lopanoic acid, and the like. When employed, substances imparting radiopacity will typically represent from about 1 to about 25 weight percent of the bone particle containing composition, calculated prior to forming the shaped material. In some embodiments, the at least partially demineralized bone may have some inherent radiopacity due to remaining mineralization.

Angiogenesis Promoting Materials

Development of a vasculature around the implant site also may help form new bone and/or cartilage tissues. Angiogenesis may be an important contributing factor for the replacement of new bone and cartilage tissues. In certain embodiments, angiogenesis is promoted so that blood vessels are formed at the site to allow efficient transport of oxygen and other nutrients and growth factors to the developing bone or cartilage tissue. Thus, angiogenesis-promoting factors may be included in the osteoimplant to increase angiogenesis in that region. For example, class 3 semaphorins, e.g., SEMA3, controls vascular morphogenesis by inhibiting integrin function in the vascular system, Serini et al., 424 Nature 391-397 (2003), incorporated herein by reference in its entirety, and may be included in the osteoimplant.

Bioactive Agents

The osteoconductive at least partially demineralized bone may provide a system for delivering bioactive agents, such as osteoinductive factors, to a host animal. Thus, the osteoimplant enables an improved healing response to the implant without the need to administer separately the bioactive agent. A problem with the introduction of the bioactive agent at the site is that it is often diluted and redistributed during the healing process by the circulatory systems (e.g., blood, lymph) of the recipient before complete healing has occurred. A solution to this problem of redistribution is to affix the bioactive components to the osteoimplant. Some bioactive agents that may be delivered using an at least partially demineralized bone composition include agents that promote the natural healing process, i.e., resorption, vascularization, angiogenesis, new growth, or the like. In one embodiment, the osteoimplant is provided in which the treated at least partially demineralized bone, together with a stabilizing agent, is used to deliver the biologically active agent. It is expected that the stabilizing agent will protect the biologically active agent from degradation, and therefore will extend its active life after delivery into the recipient animal. In certain embodiments, the bioactive agent is an osteoinductive agent, and in certain embodiments, the at least partially demineralized bone may be used to deliver more than one bioactive agent, more than two, and sometimes more than three bioactive agents. The bioactive agent may be associated with the at least partially demineralized bone. For example, the bioactive agent may be associated with the at least partially demineralized bone through electrostatic interactions, hydrogen bonding, pi stacking, hydrophobic interactions, van der Waals interactions, etc. In certain embodiments, the bioactive agent is attached to the at least partially demineralized bone through specific interactions such as those between a receptor and its ligand or between an antibody and its antigen. In other embodiments, the bioactive agent is attached to the at least partially demineralized bone through non-specific interactions (e.g., hydrophobic interactions).

Medically/surgically useful substances include physiologically or pharmacologically active substances that act locally or systemically in the host. Generally, these substances may include bioactive substances which may be readily incorporated into the osteoimplant and include, e.g., demineralized bone powder as described in U.S. Pat. No. 5,073,373, the contents of which are incorporated herein by reference in its entirety; collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as alkaline phosphatase, collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors or other means; tissue transplants; demineralized bone powder; autogenous tissues such as blood, serum, soft tissue, bone marrow, etc.; bioadhesives; BMPs; osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); IGF-1 and IGF-2; platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids. The amounts of such optionally added substances may vary widely with optimum levels being readily determined in a specific case by routine experimentation.

In certain embodiments, the agent to be delivered is adsorbed to or otherwise associated with the osteoimplant. The agent may be associated with the osteoimplant through specific or non-specific interactions; or covalent or non-covalent interactions. Examples of specific interactions include those between a ligand and a receptor, an epitope and an antibody, etc. Examples of non-specific interactions include hydrophobic interactions, electrostatic interactions, magnetic interactions, dipole interactions, van der Waals interactions, hydrogen bonding, etc. In certain embodiments, the agent is attached to the osteoimplant using a linker so that the agent is free to associate with its receptor or site of action in vivo. In certain embodiments, the agent to be delivered may be attached to a chemical compound such as a peptide that is recognized by the matrix of the at least partially demineralized bone composition. In another embodiment, the agent to be delivered is attached to an antibody, or fragment thereof, that recognizes an epitope found within the matrix of the DBM composition. In a further embodiment, the agent is a BMP, TGF-$\beta$, IGF, parathyroid hormone (PTH), growth factors, or angiogenic factors. In certain embodiments at least two bioactive agents are attached to the at least partially demineralized bone composition. In other embodiments at least three bioactive agents are attached to the at least partially demineralized bone composition.

IX. Examples

Aspects of the present teachings may be further understood in light of the following examples, which should not be construed as limiting the scope of the present teachings in any way.

Example 1

Preparation of Cancellous Dowels

Corticocancellous Dowels were drilled from the femoral condyle of a human donor using 12 mm Codman dowel cutter. Any attached cartilage or cortical bone was removed, leaving only dense and diffuse cancellous structures. The bone was drilled while in a frozen state and the drilled dowels were immediately placed in a cold solution of 0.2 mM, 1 mM NaN$_3$, and 0.1 mM Benzamidine HCl (4° C.). The bones were removed after two hours on ice. In order to remove the bone marrow elements, the dowels were lavaged using semi-gentle (nondisruptive to cancellous structure) cool water. The material was stored at −70° C. until defatting and demineralization.

Defatting and Demineralization.

The dowels were defatted in a solution of 1:1 chloroform:methanol for 15 hours at room temperature. The solution was then poured off and any organic residue was allowed to evaporate from the bone for 6 hours under a fume hood. The cancellous matrix was demineralized in 0.6 N HCl at 4° C. overnight and washed extensively with water prior to lyophilization. Specifically, the following protocol was followed:
1. Extraction with 400 ml 1:1 chloroform:methanol for 15 hours at room temperature.
2. Evaporate 6 hours under fume hood.
3. 300 ml 0.6 N HCl at 4° C. overnight.
4. Change acid, remove air bubbles by pressing cancellous structure, continue demineralization at 4° C. for 6 hours.
5. Wash with water using 800 ml at 4° C. Perform 4 times for 10 minutes each.
6. Lyophilize two dowels not treated with collagenase (one large, one small) overnight—30, 23° C. 3 days. The untreated dowels are control dowels.

Collagen Denaturation.

The collagen structure of two dowels for treatment with collagenase was gelatinized by the following sequence:
1. Extract 1 hour, 2 M CaCl$_2$ 4° C. (400 ml).
2. Wash 3×10 minutes using cold water.
3. Extract 1 hour 0.5 M EDTA pH 7.4 at 4° C. (400 ml).
4. Wash 3×10 minutes using cold water.
5. Extract 8 M LiCl overnight at 4° C. (400 ml).
6. Wash 1 hour using 400 ml water at 4° C.
7. Wash with 300 ml sterile water at 55° C. for 90 minutes.
8. Lyophilize after freezing.

The dowels so treated are referred to as bone matrix gelatin (BMG) samples.

Preparation of Samples.

Each of the dowels were cut to produce 2 long DBM of approximately 100 mg each, 2 short DBM of approximately 50 mg each, 2 long BMG of approximately 100 mg each, and 2 short BMG of approximately 60 mg each Each sample was washed and rehydrated in enough Alloprep to cover the sample (approximately 750 µl).

Collagenase Treatment.

Four samples were treated with collagenase. Two samples were BMG samples. Two samples were DBM samples.

Materials:
Digestion buffer (50 mM Tris-HCl pH 7.4, containing 5 mM CaCl$_2$, sterile filtered);
Chromatographically purified collagenase (Worthington CLSPA; Source: *Clostridium Histolyticum*; 10,000 units); and
0.1N Glacial acetic acid (Add 248.56 ml of deionized water to 1.44 ml of 17.4 M Glacial Acetic Acid, Sterile filtered).

Generally, collagenase treatment comprised placing sections of demineralized cancellous dowels weighing between 50 and 100 mg in a 5 ml digestion buffer containing 80 units/ml collagenase. The samples were incubated at 37° C. for 90 minutes. Each sample was washed for 30 minutes with 30 ml 0.1N acetic acid in the cold. The samples were then rinsed for 10 minutes with phosphate buffered saline ("PBS") and 10 minutes with deionized water prior to lyophilization. The specific protocol was as follows:
1. Cut 2 cancellous BMG pieces, one from the BMG-long which weighed 100 mg and one from the BMG-short which weighed 60 mg.

2. Cut 2 cancellous DBM pieces, one from the DBM-long which weighed 100 mg and one from the DBM-short which weighed 50 mg.
3. Add 4.8 ml digestion buffer to each sample.
4. Add 200 μl of stock collagenase to each sample.
5. Vortex each sample.
6. Incubate each sample for 1.5 hours in a 37° C. water bath.
7. Add 30 ml 0.1N glacial acetic acid to each sample. Wash for 1 hour at 4° C. using a magnetic stir bar and plate.
8. Pour off the glacial acetic acid.
9. Wash with 45 ml PBS for 10 minutes at 4° C. Pour off PBS. Repeat.
10. Wash with 45 ml deionized water for 10 minutes at 4° C. Pour off deionized water.
11. Press samples into a syringe and freeze-dry using a 24 hour cycle.

Implantation.

The following pieces were implanted, aiming for a range of 10-20 mg (all samples were implanted in athymic rats except for those where mouse is indicated):

| Collagenase short-BMG | Collagenase long-BMG |
|---|---|
| 9 mg | 14 mg |
| 8 mg | 17 mg |
| 12 mg | 18 mg |
| 14 mg (mouse) | |

| Collagenase short-DBM | Collagenase long-DBM |
|---|---|
| 7 mg | 11 mg |
| 9 mg | 17 mg |
| 18 mg | 18 mg |
| 9 mg (mouse) | |

| Control Short BMG | Control Long BMG |
|---|---|
| 10 mg | 10 mg |
| 11 mg | 10 mg |
| 12 mg | 11 mg |

| Control Short DBM | Control Long DBM |
|---|---|
| 10 mg | 10 mg |
| 10 mg | 11 mg |
| 11 mg | 12 mg |

Assay.

The osteoinductive potential of collagenase treated and untreated (control) cancellous bone samples was evaluated by implanting the materials intramuscularly in athymic rats and an athymic mouse. After 28 days the explants were evaluated histologically and radiographically for evidence of heterotopic bone formation.

Results.

FIG. 1 is a graph illustrating the results of Example 1. As shown, the collagenase treated DBM had higher histologic scores for both the long and short samples than did the control DBM. The long collagenase treated BMG sample had a lower histologic score than did the long control BMG sample. The short collagenase treated BMG sample had a higher histologic score than did the short control BMG sample.

The results demonstrate that collagenase treatment enhances the osteoinductive activity of cancellous DBM scaffolds. More specifically, the results indicate that the osteinductive activity of cancellous DBM scaffolds, as measured by the histologic score, was measurable, and increased above that of untreated DBM, in all samples. The increase may be noted both histologically and radiographically. Collagenase treated human demineralized cancellous scaffolds have potent osteoinductive activity as measured by heterotopic bone formation in athymic rats. The negligble osteoinductive activity of human cancellous demineralized scaffolds in athymic mice may be markedly enhanced by treatment with bacterial collagenase, without requiring treatment with LiCl prior to treatment with bacterial collagenase. The activity of these preparations is comparable to that of human cortical DBM.

Example 2

Cancellous bone was demineralized in 0.6 N HCl at room temperature. The demineralized bone was washed, and the wet demineralized bone was smeared to a consistency of a fibrous paste. The fibrous paste was then treated using one of three methods:
1. Hand manipulated with slight pressure, dried at ambient temperature for approximately 72 hours;
2. Placed in a PTFE mold and compressed between plungers. The loaded hand clamped mold was placed in a vacuum oven and dried at 40° C. for approximately 72 hours;
3. Loaded into a mold and compressed between stainless steel dehydrothermal plungers. Initially, 500 pounds of force was applied to the plungers to press out excess water and compress the paste. After initial compression, dead weights were applied to continue to keep the paste under compression while a vacuum was drawn through the dehydrothermal plunters. During vacuum drying (via the plungers), the mold was kept at approximately 40° C. for 72 hours.

Figure 3:
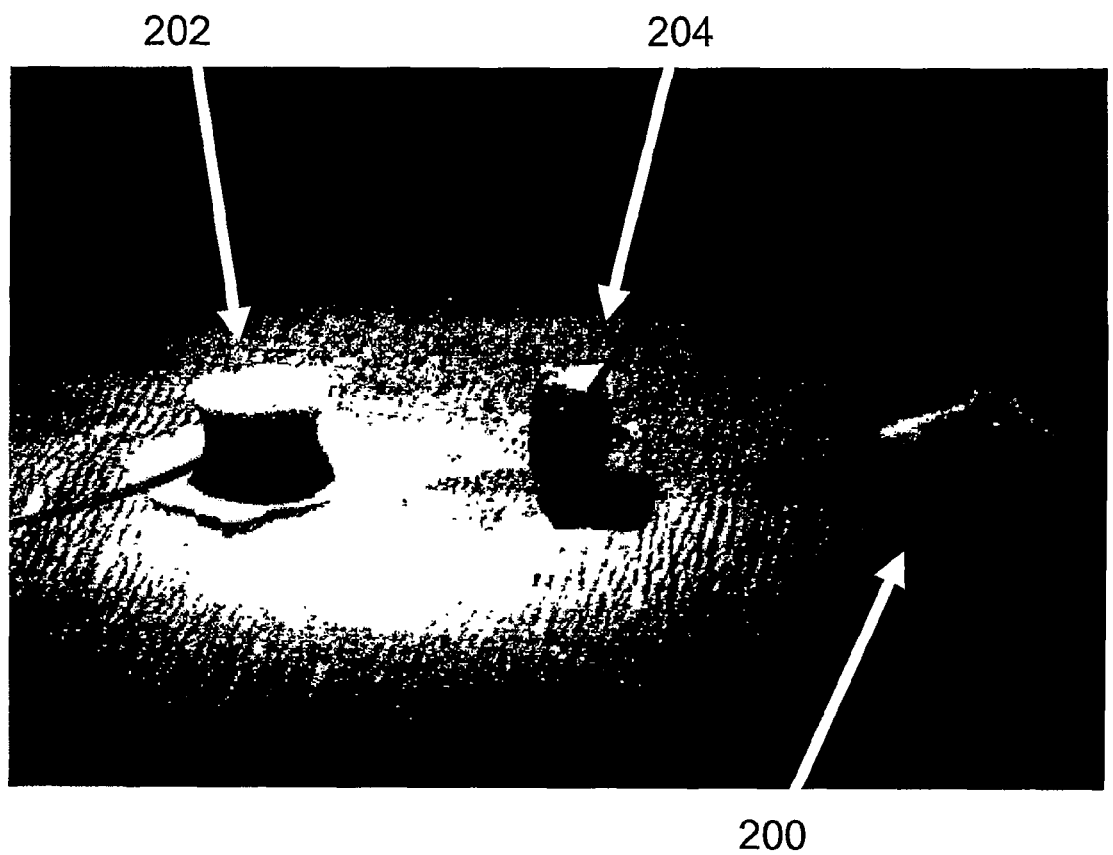
FIG. 3 illustrates formulations of compressed DBM.
Figure 4:
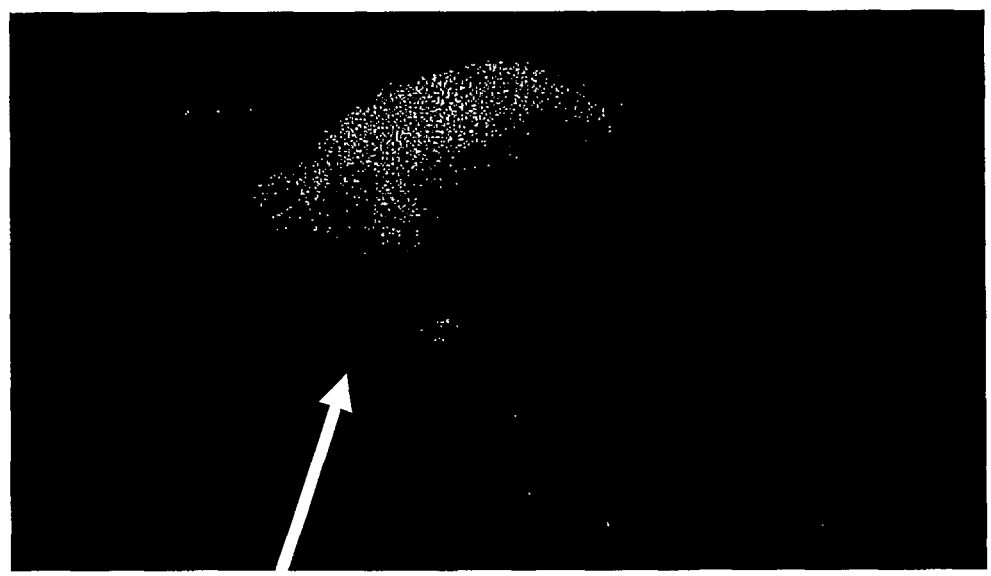
FIG. 4 illustrates a formulation of FIG. 3 after 7 hours of submersion in water.
Figure 5:
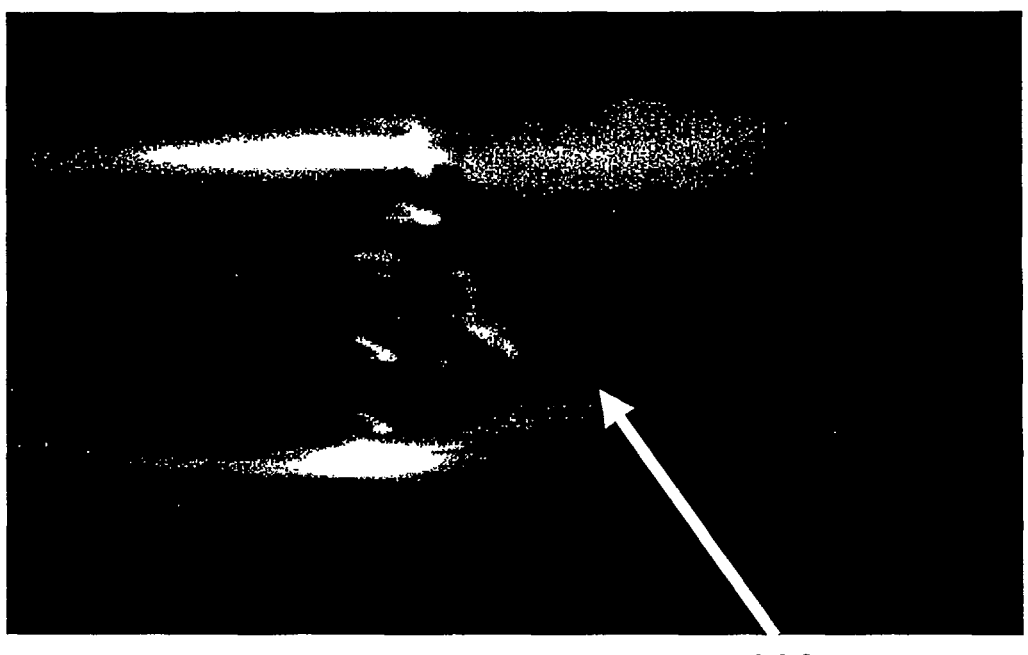
FIG. 5 illustrates a formulation of FIG. 3 after 72 hours of submersion in water.
Figure 6:
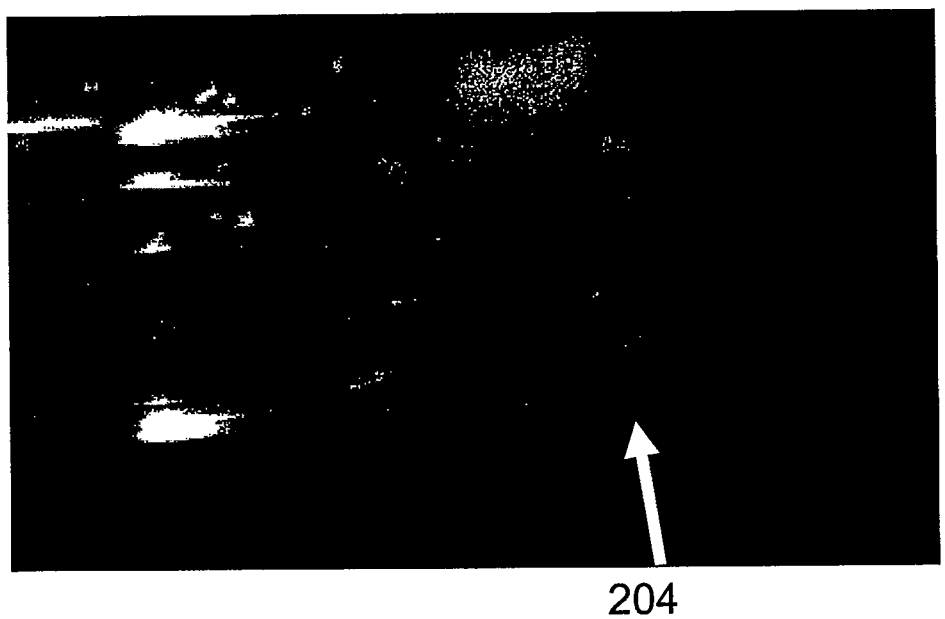
FIG. 6 illustrates a formulation of FIG. 3 after 7 hours of submersion in water.

After processing, each sample was placed in a beaker containing room temperature deionized water, and observed for signs of disassociation. FIG. 3 illustrates the formulations thus produced. Formulation 200 corresponds to method 1, formulation 202 corresponds to method 2, and formulation 204 corresponds to method 3. Each of the formulations 200, 202, and 204 were submerged in deionized water and observed for cohesiveness. FIG. 4 illustrates formulation 200 at 7 hours of submersion in water. FIG. 5 illustrates formulation 202 submerged in water for 72 hours. FIG. 6 illustrates formulation 204 submerged in water for 72 hours. From FIG. 4, formulation 200 swelled when submerged in water but did not dissociate. From FIGS. 5 and 6, formulations 202 and 204 each generally retained their shape in water.

X. Assessment of Osteogenic Activity

Induction of bone formation may be determined by a histological evaluation showing the de novo formation of bone with accompanying osteoblasts, osteoclasts, and osteoid matrix. For example, osteoinductive activity of an osteoinductive factor may be demonstrated by a test using a substrate onto which material to be tested is deposited. The substrate with deposited material is implanted subcutaneously in a test animal. The implant is subsequently removed and examined microscopically for the presence of bone formation including the presence of osteoblasts, osteoclasts, and osteoid matrix. A suitable procedure for assessing osteoinductive activity is illustrated in Example 5 of U.S. Pat. No. 5,290,763 ("the '763 patent"), herein incorporated by reference in its entirety. Although there is no generally accepted scale of evaluating the degree of osteogenic activity, certain factors are widely recognized as indicating bone formation. Such factors are referenced in the scale of 0-8 which is provided in Table 3 of example 1 of U.S. Pat. No. 5,563,124, herein incorporated by reference in its entirety. The 0-4 portion of this scale corresponds to the scoring system described in the '763 patent, which is limited to scores of 0-4. The remaining portion of the scale, scores 5-8, references additional levels of maturation of bone formation. The expanded scale also includes consideration of resorption of collagen, a factor which is not described in the '763 patent.

Human DBM has not been proven to have osteoinductive activity in higher order species. Studies indicate that dog DBM is osteoinductive when tested in athymic rats but not in dogs. Further, studies have been published stating that BMP-2 has osteoinductive activity in squirrel monkeys but bone matrix does not. Collagenase treated DBM slowly solubilizes in tissue culture media (in the presence of cells) at 37° C. Without being bound by theory, it is possible that the lack of osteoinductive activity of DBM in higher species may be related to the failure of DBM to present growth factors to the host in an efficient manner. Collagenase treatment provides a DBM capable of osteoinductive activity in higher species. Such formation may serve as a basis for eliminating the need for autograft in many orthopaedic applications, including posterior spinal fusion.

XI. Uses

The osteogenic osteoimplant is intended to be applied at a bone repair site, for example, a site resulting from injury, defect brought about during the course of surgery, infection, malignancy, or developmental malformation. The osteoimplant may be utilized in a wide variety of orthopaedic, periodontal, neurosurgical, and oral and maxillofacial surgical procedures.

Demineralized cancellous bone has a sponge-like structure. The material may be compressed significantly and will substantially regain its original structure in the absence of the compressive force. An osteoinductive cancellous scaffold may be forced into a space or defect through a small opening. The structure will then expand and conform to the shape of the environment. This characteristic may be particularly useful in embodiments wherein the collagenous structure has been altered, for example, by treatment with collagenase. Thus, in one application, an osteoinductive cancellous scaffold is placed into a compromised vertebral element in a procedure similar to vertebroplasty. It is expected that the cancellous scaffold would expand in the collapsed vertebrae and, over time, new bone formed in the interior of the vertebral element would restore its structural integrity. The procedure could be used in conjunction with or as a replacement for Kyphoplasty.

In addition or alternatively, demineralized cancellous bone may be ground into a particulate and formed into a compressed implant having a denser structure compared to the implant described above. The dense implant may be used alone or in combination with implant scaffolding. The implant may expand in vivo over the course of between a few hours to a few weeks depending on, for example, the density of the implant, other materials incorporated into the compressed implant, the size and shape of the implant, or other aspects of the implant that would be readily understandable by those skilled in the art.

At the time just prior to when the osteoimplant of the invention is to be placed in a defect site, optional materials, e.g., autograft bone marrow aspirate, autograft bone, preparations of selected autograft cells, autograft cells containing genes encoding bone promoting action, etc., may be combined with the osteoimplant. The osteoimplant may be implanted at the bone repair site, if desired, using any suitable affixation means, e.g., sutures, staples, bioadhesives, screws, pins, rivets, other fasteners and the like, or it may be retained in place by the closing of the soft tissues around it.

Activated scaffolds comprising the osteoinductive cancellous DBM may reduce or eliminate the need for harvesting iliac crest autograft in challenging orthopaedic applications such as posterolateral spinal fusion and the treatment of critical sized nonunion fractures.

The osteoinductive at least partially demineralized bone may also be used as a drug delivery device. Demineralized cancellous bone has the capacity to absorb significant amounts of fluids, and it has a high surface area to volume ratio. These properties indicate that the material would be an ideal growth scaffold for bioactive cells. Osteoinductive at least partially demineralized bone may be used as a carrier for osteogenic cells, chrondrogenic cells, stem cells, bone marrow aspirates, fat cells, and other cell types that are involved in tissue formation or that have the capability to differentiate into tissue forming cells when exposed to appropriate signals. The at least partially demineralized bone may also serve as a carrier for a variety of native or recombinant growth and differentiation factors.

Collagenase treatment of at least partially demineralized bone may have further applications. For example, cells harvested from a recipient may be treated with collagenase treated at least partially demineralized bone in a manner that induces their differentiation into bone, cartilage, or other types of tissues such as bone marrow, neural cells, or vasculature. The tissues/organs could then be transplanted into the recipient after they have developed to a certain point in vitro. In addition, at least partially demineralized bone contains a variety of growth factors. The type of growth factors harvested, and the manipulation of cell culture conditions or specific growth factor levels in at least partially demineralized bone, may be optimized for the tissue of interest.

In certain embodiments, association with the osteoinductive at least partially demineralized bone increases the half-life of the relevant biologically active agent(s). Certain inventive drug delivery devices are used to deliver osteoinductive growth factors. Other agents that may be delivered include factors or agents that promote wound healing. However, the osteoinductive at least partially demineralized bone may alternatively or additionally be used to deliver other pharmaceutical agents including antibiotics, anti-neoplastic agents, growth factors, hematopoietic factors, nutrients, an other bioactive agents described above. The amount of the bioactive agent included with the at least partially demineralized bone composition can vary widely and will depend on such factors as the agent being delivered, the site of administration, and the patient's physiological condition. The optimum levels is determined in a specific case based upon the intended use of the implant.

XII. Conclusion

In certain embodiments, the osteoinductive at least partially demineralized bone and associated osteoimplants produce bone or cartilage in an animal model and/or in human patients with similar timing and at a level at least 10%, 20%, 35%, 50%, 100%, 200%, 300%, or 400% or greater osteogenic, osteoinductive or chondrogenic activity than a corollary at least partially demineralized bone that has not been exposed to a treatment or condition as described herein. Of course, one skilled in the art will appreciate that these values may vary depending on the type of test used to measure the osteoinductivity or osteogenic or chondrogenic activity described above. The test results may fall within the range of 10% to 35%, 35% to 50%, 50% to 100%, 100% to 200%, and 200% to 400%. In certain embodiments, when an osteoimplant is implanted into a bone defect site, the osteoimplant has an osteoinductivity score of at least 1, 2, 3, or 4 in an animal model and/or in humans. In some embodiments, when an osteoimplant comprising osteoinductive cancellous DBM is implanted in a bone defect site, the osteoimplant has an osteoinductivity score comparable to a cortical DBM implant that has not been treated.

Although the invention has been described with reference to various embodiments, persons skilled in the art will recognize that changes may be made in form and detail without departing from the spirit and scope of the invention.

What is claimed is:

1. An osteoinductive composition comprising:
   a compacted cancellous bone structure, wherein the cancellous bone is at least partially demineralized cancellous bone, the at least partially demineralized cancellous bone having been treated with collagenase to digest or modify collagen fibers of said cancellous bone and increase the osteoinductive activity of the bone;
   wherein the compacted, at least partially demineralized cancellous bone exhibits increased osteoinductive activity when compared to untreated at least partially demineralized cancellous bone.

2. The osteoinductive composition of claim 1, wherein the composition has a histologic osteoinductivity score of at least 1 on a 4 point scale.

3. The osteoinductive composition of claim 1, wherein the composition induces bone formation in higher order species.

4. The osteoinductive composition of claim 1, wherein the composition exhibits a solid structure at room temperature and substantially liquefies when implanted in a body.

5. The osteoinductive composition of claim 1, wherein the composition has enhanced solubility when compared to solubility of untreated at least partially demineralized bone matrix.

6. The osteoinductive composition of claim 1, wherein the trabecular structure of the treated at least partially demineralized cancellous bone is compacted when compared to trabecular structure of untreated at least partially demineralized cancellous bone.

7. The osteoinductive composition of claim 1, wherein the at least partially demineralized cancellous bone exhibits a trabecular density that is increased when compared to untreated at least partially demineralized cancellous bone.

8. The osteoinductive composition of claim 1, wherein at least 25% of the collagen fibers of the treated at least partially demineralized cancellous bone are digested or modified when compared to collagen of untreated at least partially demineralized cancellous bone.

9. The osteoinductive composition of claim 1, wherein at least 50% of the collagen fibers of the treated at least partially demineralized cancellous bone are digested or modified.

10. The osteoinductive composition of claim 1, wherein the at least partially demineralized cancellous bone is compacted and wherein the composition retains its shape in water for a predetermined period of time.

11. The osteoinductive composition of claim 1, wherein the at least partially demineralized cancellous bone is particulated and reformed into an implant.

12. The osteoinductive composition of claim 11, wherein the implant further comprises a carrier.

13. The osteoinductive composition of claim 12, wherein the carrier is a polymer and wherein the cancellous bone is treated after blending with the polymer.

14. The osteoinductive composition of claim 1, further comprising at least partially demineralized cortical bone that has been treated to increase the osteoinductive activity of the bone.

15. The osteoinductive composition of claim 1, further comprising at least partially demineralized corticocancellous bone that has been treated to increase the osteoinductive activity of the bone.

16. The osteoinductive composition of claim 1, further comprising a bioactive agent.

17. The osteoinductive composition of claim 1, wherein native inductive materials of the at least partially demineralized bone matrix are substantially exposed.

18. The osteoinductive composition of claim 1, further comprising at least one inductive material.

19. The osteoinductive composition of claim 1, wherein the demineralized cancellous bone is further exposed to a chemical treatment.

20. The osteoinductive composition of claim 19, wherein the chemical is chosen from the group consisting of cyanogen bromide, guanidinium HCl, alkylating agents, and lithium chloride.

21. An osteoinductive composition comprising:
   a compacted cancellous bone structure, wherein the cancellous bone is at least partially demineralized cancellous bone, the at least partially demineralized cancellous bone having been treated with collagenase to alter the structure of collagen and increase the osteoinductive activity of the bone;
   wherein the compacted, at least partially demineralized cancellous bone exhibits increased osteoinductive activity when compared to untreated at least partially demineralized cancellous bone.

* * * * *

UNITED STATES PATENT AND TRADEMARK OFFICE
CERTIFICATE OF CORRECTION

PATENT NO. : 8,734,525 B2
APPLICATION NO. : 12/140025
DATED : May 27, 2014
INVENTOR(S) : Behnam et al.

Page 1 of 1

It is certified that error appears in the above-identified patent and that said Letters Patent is hereby corrected as shown below:

On the Title Page, in Item [75], delete "John Winterbottom," and insert -- John M. Winterbottom, --, therefor.

On the Title Page, in Item [75], delete "Todd Boyce," and insert -- Todd M. Boyce, --, therefor.

On the Title Page, in Item [56], in Column 2, Line 6, delete "osteobalst-like" and insert -- osteoblast-like --, therefor.

On the Title Page, in Item [56], in Column 2, Lines 35-36, delete "Boen for Repair of Diaphyseal Boen" and insert -- Bone for Repair of Diaphyseal Bone --, therefor.

In the Specification

Column 5, Line 48, delete "Substances" and insert -- Substances: --, therefor.

Column 13, Line 24, delete "Lewandroski et al.," and insert -- Lewandrowski et al., --, therefor.

Column 18, Line 16, delete "network." and insert -- network, --, therefor.

Column 32, Lines 7-8, delete "osteinductive" and insert -- osteoinductive --, therefor.

Column 32, Line 41, delete "plunters." and insert -- plungers. --, therefor.

Signed and Sealed this
Twenty-sixth Day of August, 2014

Michelle K. Lee
*Deputy Director of the United States Patent and Trademark Office*